(12) United States Patent
Magnuson

(10) Patent No.: US 10,881,135 B1
(45) Date of Patent: Jan. 5, 2021

(54) CYCLONICALLY COOLED AND FILTERED SMOKING WATER PIPE AND METHOD

(71) Applicant: Robert S Magnuson, Spokane, WA (US)

(72) Inventor: Robert S Magnuson, Spokane, WA (US)

(73) Assignee: Creative Destruction, LLC, Spokane, WA (US)

( * ) Notice: Subject to any disclaimer, the term of this patent is extended or adjusted under 35 U.S.C. 154(b) by 188 days.

(21) Appl. No.: 15/809,321

(22) Filed: Nov. 10, 2017

(51) Int. Cl.
| | |
|---|---|
| *A24F 1/02* | (2006.01) |
| *A24F 1/30* | (2006.01) |
| *A61M 15/00* | (2006.01) |
| *B01F 3/04* | (2006.01) |
| *B01F 13/08* | (2006.01) |

(52) U.S. Cl.
CPC ............ *A24F 1/02* (2013.01); *A24F 1/30* (2013.01); *A61M 15/0006* (2014.02); *A61M 15/0086* (2013.01); *B01F 3/04531* (2013.01); *B01F 13/0818* (2013.01)

(58) Field of Classification Search
CPC .... A24F 1/02; A24F 1/32; A24F 7/02; A61M 15/0006; A61M 15/0086
See application file for complete search history.

(56) References Cited

U.S. PATENT DOCUMENTS

| | | | |
|---|---|---|---|
| 3,932,068 A | 1/1976 | Zimmermann | |
| 3,938,914 A | 2/1976 | Zimmermann | |
| 4,023,738 A | 5/1977 | Ogihara et al. | |
| 4,040,605 A | 8/1977 | Towsend | |
| 4,134,553 A | 1/1979 | Steinort et al. | |
| 4,134,557 A | 1/1979 | Lazzari et al. | |
| 4,162,875 A | 7/1979 | Lux et al. | |
| 4,266,914 A | 5/1981 | Dickinson | |
| 4,498,785 A | 2/1985 | de Bruyne | |

(Continued)

OTHER PUBLICATIONS

Vermont Veterinary Cardiology Services, "Velocity and pressure Distribution for Flow over a Cylinder", pulled from the internet at http://www.vermontveterinarycardiology.com/index.php/for-cardiologists/for-cardiologists?id=127 on Jan. 20, 2020 (Year: 2020).*

*Primary Examiner* — Alex B Efta
(74) *Attorney, Agent, or Firm* — Wells St. John P.S.; Keith D. Grzelak

(57) ABSTRACT

A hydrodynamically cooled and filtered smoking apparatus is provided having a housing, an inlet pipe, a stirring mechanism, and a flow deflecting body. The housing having at least one wall portion providing a chamber configured to contain a fluid for circulation therein. The inlet pipe has an inlet configured to draw in smoke from a source and an outlet provided within the chamber beneath a top surface of the contained fluid configured to deliver the smoke into the chamber for entrainment within the fluid. The stirring mechanism is provided in the housing and is driven to induce cyclonic circulation of the fluid and the smoke in the chamber. The flow deflecting body has a suction surface with at least one aperture provided in the suction surface and communicating with the inlet pipe. The suction surface is oriented in the fluid to generate hydrodynamic force to draw smoke into the fluid and aerate the fluid by entraining the smoke in the fluid as bubbles. A method is also provided.

20 Claims, 21 Drawing Sheets

(56) References Cited

U.S. PATENT DOCUMENTS

| | | | |
|---|---|---|---|
| 4,588,577 A | 5/1986 | Cardinal | |
| 5,078,969 A | 1/1992 | Bacus | |
| 5,240,322 A | 8/1993 | Haber et al. | |
| 5,407,272 A | 4/1995 | Meier | |
| 5,547,280 A | 8/1996 | Wanninger et al. | |
| 5,586,823 A | 12/1996 | Carr | |
| 6,095,677 A | 8/2000 | Karkos, Jr. et al. | |
| 6,210,033 B1 | 4/2001 | Karkos, Jr. et al. | |
| 6,336,603 B1 | 1/2002 | Karkos, Jr. et al. | |
| 6,354,301 B2 | 3/2002 | McCoy | |
| 6,715,494 B1 | 4/2004 | McCoy | |
| 6,793,167 B2 | 9/2004 | Karkos, Jr. et al. | |
| 6,872,362 B2 | 3/2005 | Schmidt et al. | |
| 7,211,430 B2 | 5/2007 | Schwarz et al. | |
| 7,288,229 B2 | 10/2007 | Turner et al. | |
| 7,575,184 B2 | 8/2009 | Reed et al. | |
| 8,201,765 B2 | 6/2012 | Rajagopal et al. | |
| 8,356,763 B2 | 1/2013 | Rajagopal et al. | |
| 10,321,714 B1 * | 6/2019 | Kane | H02J 7/00 |
| 2003/0197080 A1 * | 10/2003 | Karkos, Jr. | A23G 9/045 241/92 |
| 2016/0295911 A1 * | 10/2016 | Kalousek | A24F 1/30 |

\* cited by examiner

CYCLONICALLY COOLED AND FILTERED SMOKING WATER PIPE AND METHOD

TECHNICAL FIELD

This disclosure pertains to devices for mixing a gas with a fluid in order to cool the gas. More particularly, this disclosure relates to apparatus and methods for cooling a smoking pipe with water.

BACKGROUND OF THE INVENTION

Techniques are known for mixing a gas with water to cool the gas for further use or processing. For the case of therapeutic or medicinal smoking of burning, dried plant materials, it is often the case that a user has one or more physical conditions that will be irritated or exacerbated by the intake of hot smoke into their respiratory system. There exists a need to further improve the manner in which such smoke is cooled in order to reduce irritation to a user or medical patient. Other mixing and cooling applications could further benefit from a solution to this need.

SUMMARY OF THE INVENTION

An apparatus and method are provided for mixing one or more gases with a fluid in order to cool the gas, such as mixing a smoked-entrained air mixture within a bath of circulating fluid in order to cool the air mixture, after which the cooled smoke-entrained air mixture is collected and drawn off for subsequent use. In one case, the apparatus is a cyclonically cooled and filtered smoking apparatus, or water pipe having a chamber of cooling fluid and a hydrodynamic flow deflecting body that draws a smoke-entrained air mixture using smoke from a dried plant material, such as tobacco or cannabis, into the fluid for dispersal and cooling, and subsequent collection by a user According to one aspect, a hydrodynamically cooled and filtered smoking apparatus is provided having a housing, an inlet pipe, a stirring mechanism, and a flow deflecting body. The housing has at least one wall portion providing a chamber configured to contain a fluid for circulation therein. The inlet pipe has an inlet configured to draw in smoke from a source and an outlet provided within the chamber beneath a top surface of the contained fluid configured to deliver the smoke into the chamber for entrainment within the fluid. The stirring mechanism is provided in the housing and is driven to induce circulation of the fluid and the smoke in the chamber. The flow deflecting body has a suction surface with at least one aperture provided in the suction surface and communicating with the inlet pipe. The suction surface is oriented in the fluid to generate aerodynamic force to draw smoke into the fluid and aerate the fluid by entraining the smoke in the fluid as bubbles.

According to another aspect, a cyclonically cooled and filtered smoking water pipe is provided having a housing, an inlet pipe, a surface portion attached thereto, a static port, and a stirring mechanism. The housing has a chamber configured to contain a liquid for cyclonic circulation therein. The inlet pipe has an inlet for drawing in a smoke and an outlet provided within the chamber so as to be entrained in a fluid bath therein. The surface portion is provided in fluid communication with fluid in cyclonic circulation within the chamber. The static port is provided in the surface portion and communicates with the inlet pipe. The surface portion is oriented in the fluid to generate a vacuum on the inlet pipe to draw smoke into the fluid and entrain the smoke in the fluid as bubbles. The stirring mechanism is provided in the housing and is driven to induce cyclonic circulation of the fluid and the smoke in the chamber.

According to yet another aspect, a method is provided for cooling smoke in a liquid. The method includes: providing a housing having a chamber filled with fluid, a surface portion having at least one static port contiguous with a source of heated smoke and in fluid communication with the fluid, and a stirring mechanism provided in the chamber; imparting movement of the fluid in the chamber with the stirring mechanism; drawing smoke from the source through the at least one static port for entrainment and mixing in the fluid; and cooling the smoke by entraining and mixing the smoke with the fluid through movement of the fluid in the chamber.

BRIEF DESCRIPTION OF THE DRAWINGS

Preferred embodiments of the disclosure are described below with reference to the following accompanying drawings.

DETAILED DESCRIPTION OF THE PREFERRED EMBODIMENTS

This disclosure is submitted in furtherance of the constitutional purposes of the U.S. Patent Laws "to promote the progress of science and useful arts" (Article 1, Section 8).

The terms "a", "an", and "the" as used in the claims herein are used in conformance with long-standing claim drafting practice and not in a limiting way. Unless specifically set forth herein, the terms "a", "an", and "the" are not limited to one of such elements, but instead mean "at least one".

Figure 1:
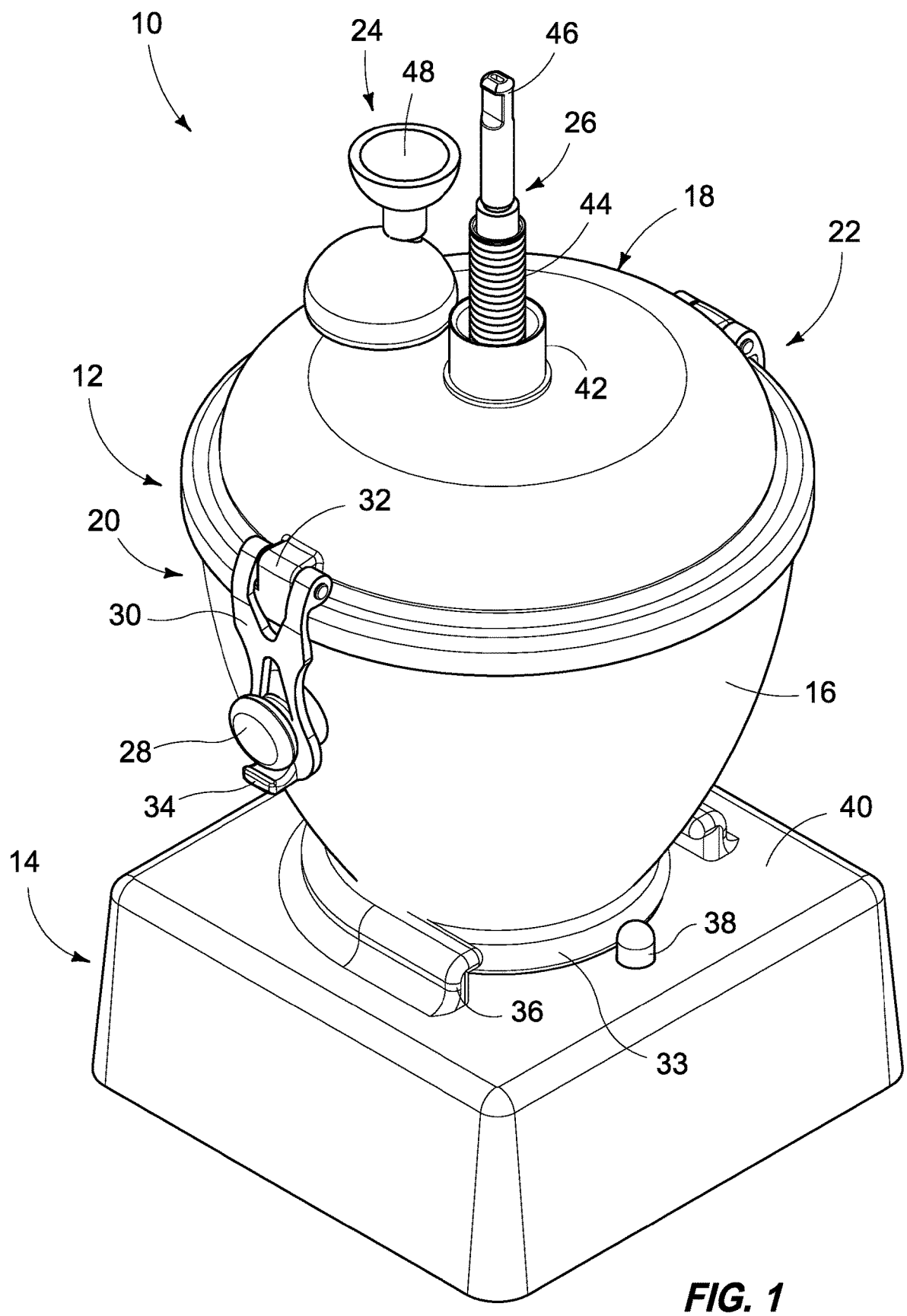
FIG. 1 is a perspective view from above illustrating a cyclonically cooled and filtered water pipe according to a first embodiment.
Figure 2:
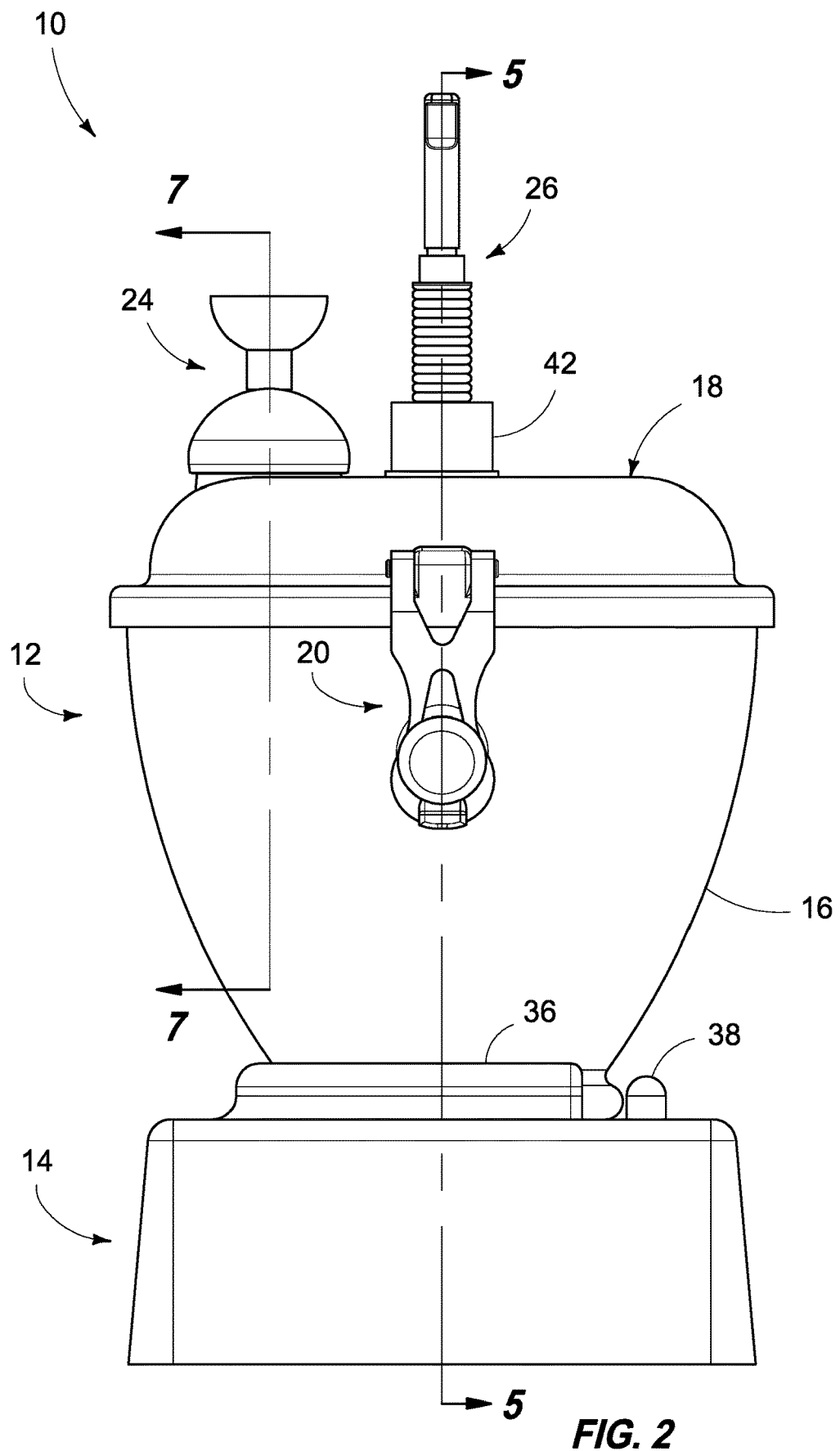
FIG. 2 is a left side elevational view of the water pipe of FIG. 1.
Figure 3:
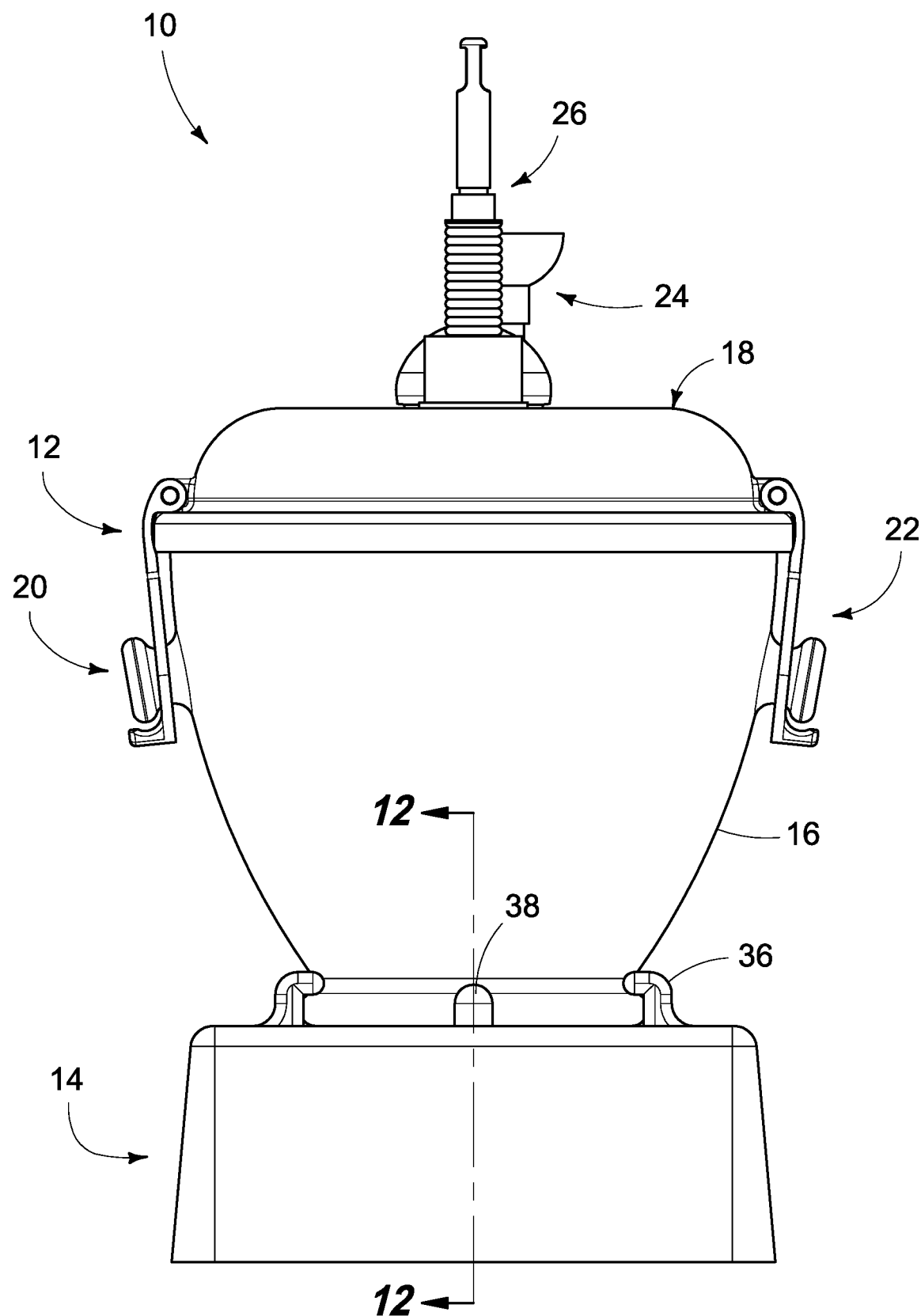
FIG. 3 is a front elevational view of the water pipe of FIGS. 1 and 2.
Figure 4:
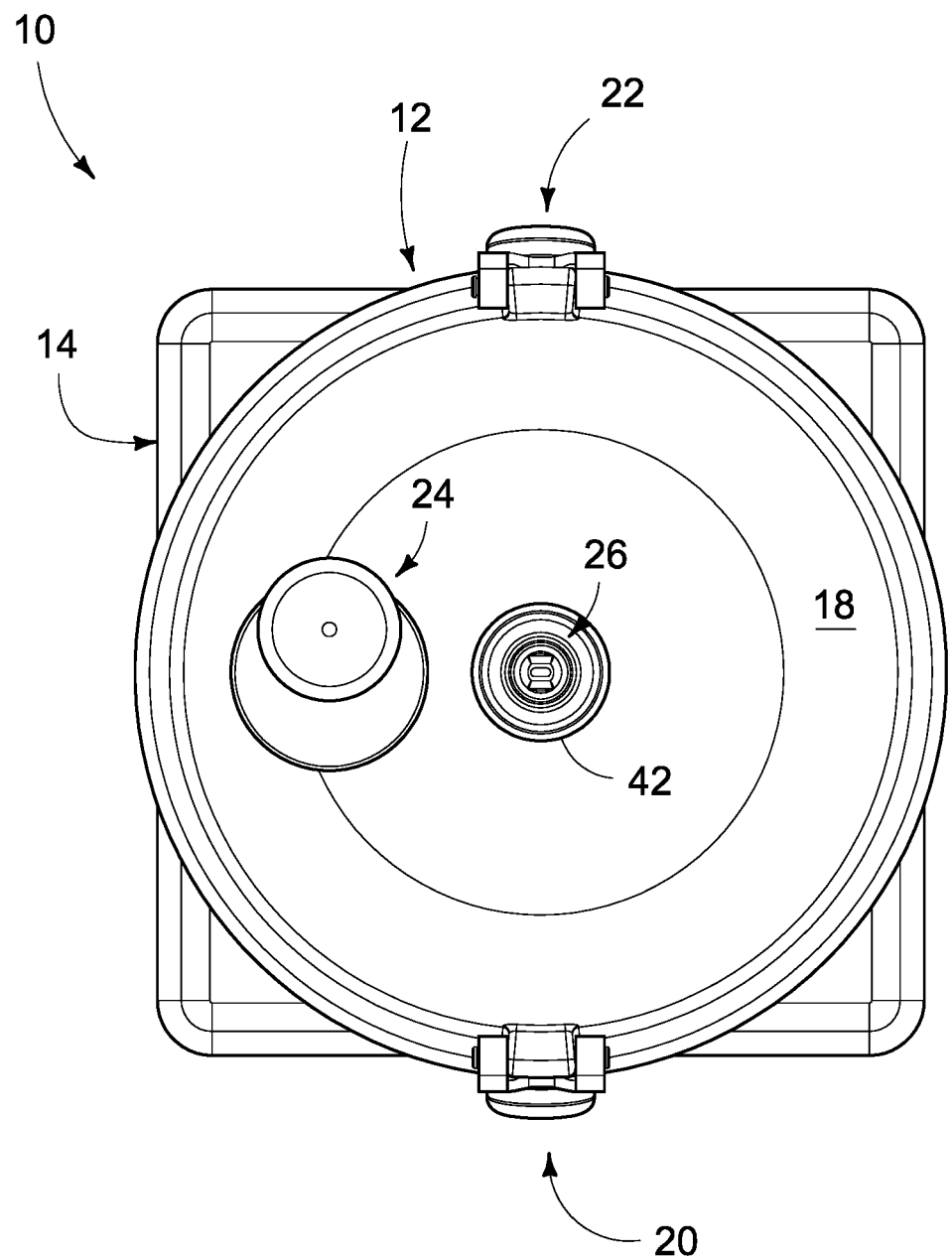
FIG. 4 is a plan view from above of the water pipe of FIGS. 1-3.

FIG. 1 illustrates a smoking apparatus in the form of a cyclonically cooled and filtered water pipe according to a first embodiment, as shown in FIGS. 1-13 and identified by reference numeral 10. As shown in FIG. 1, smoking apparatus 10 includes a bowl assembly 12 that is removably received atop a motorized base 14 to drive mixing of smoke and water within a bowl 16 of bowl assembly 12. A cover 18 is releasably retained atop bowl 16 using a pair of diametrically opposed cover latch assemblies 20 and 22. A smoke and ash filtration apparatus 24 and a smoke withdrawal apparatus 26 are provided in cover 18. Dried plant material, such as tobacco or cannabis, are deposited in a semi-spherical input bowl 48 of filtration apparatus 24 where the material is burned, generating smoke that is drawing within bowl 16. A mouthpiece 46 on smoke withdrawal apparatus 26 is provided at an output end of a flexible and extendible coil hose 44 that extends through cover 18 via an exit port 42. A user withdraws cooled smoke, received from bowl 48, via mouthpiece 46, after such smoke has been desirably cyclonically cooled and filtered within bowl 16 of smoking apparatus, or water pipe 10.

According to FIG. 1, cover 18 is removably affixed atop bowl 16 with cover latch assemblies 20 and 22 in order to facilitate cleaning of related components of smoking apparatus 10, including bowl 16, cover 18, filtration apparatus 24, and smoke withdrawal apparatus 26. More particularly, cover latch assembly 20 includes a short post, or bollard 28 having an enlarged head and narrowed neck and a stretchable, elastic strap 30. Strap 30 is affixed to cover 18 via a support block 32 integrally formed with cover 18 using a steel pin, or rivet 64 (see FIG. 5) that passes through a complementary set of bores in strap 30 and respective bore in block 32.

Figure 5:
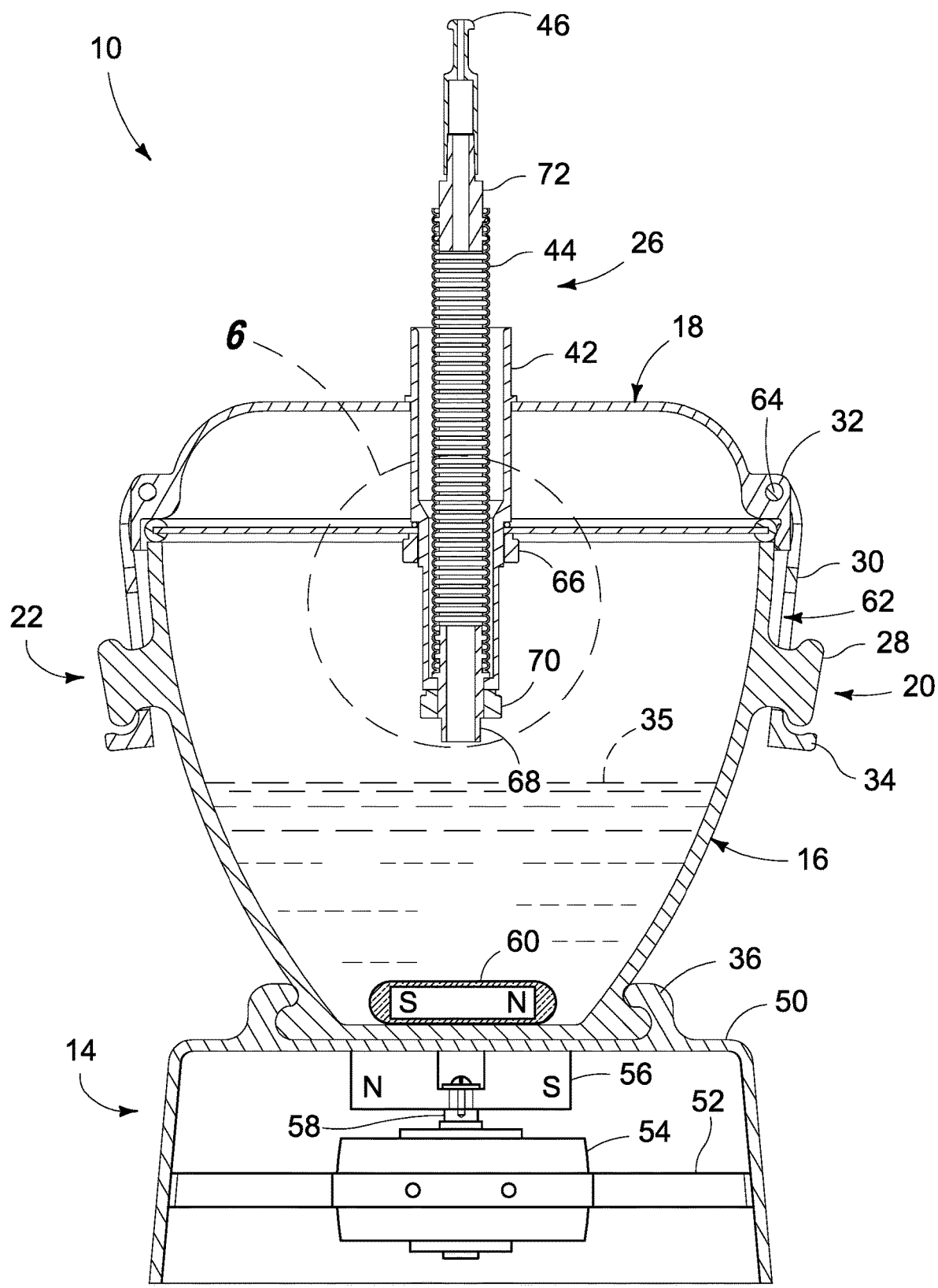
FIG. 5 is a vertical sectional view taken along line 5-5 of FIG. 2 illustrating the outlet port and expandable hose assembly.

According to one construction, strap 30 of FIGS. 1 and 5 is constructed from an elastic material, such as a natural rubber or synthetic rubber material. Optionally, strap 30 can comprise any form of suitable stretchable material, such as plastics that have suitable elastomeric properties sufficient to enable stretching of strap 30 over post 28, including thermoplastic polyether, such as TPU 90A, so that an aperture 62 (see FIG. 5) stretches over an enlarged head of post 28. An integrally formed end tab 34 on strap 30 facilitates tactile manipulation and stretching of strap 30 over and about post 28 for securement of cover latch assembly 20, as shown in FIG. 5. Such tab also facilitates tactile manipulation of strap 30 during removal from post 28. Cover latch assembly 22 (of FIGS. 1 and 5) is constructed in an identical manner as cover latch assembly 20. Optional constructions for a latch assembly are also possible which are suitable to removably affixing cover 18 atop bowl 16, such as shown in the embodiment of FIGS. 14-22.

Also depicted in FIG. 1, the assembly of bowl 16 and cover 18 is removably affixed atop base 14 via a horseshoe-shaped lip flange 36 that is integrally molded atop a top housing surface 40 of base 14. A complementarily shaped cylindrical flange 33 is provided integrally formed along a bottom end of bowl 16 for mating and demating with lip flange 36 of base 14 to facilitate mounting and demounting of bowl 16 from base 14 to facilitate cleaning and assembly/disassembly of components accompanying bowl 16 and cover 18. A latch assembly 38 comprising a spring-mounted plunger pin retains bowl 16 to base 14 when flange 33 is received within flange 36. Further details of latch assembly 38 are described below with reference to FIGS. 12-13. Further details of latches 20 and 22, filtration apparatus 24, smoke withdrawal apparatus 26, and securement of bowl 16 to base 14 with flanges 33 and 36 and latch assembly 38 are further depicted variously in FIGS. 2-4 and 8.

According to one construction, base 14, bowl 16, and cover 18 can be constructed of molded plastic. Optionally, such components can be constructed from glass, composite, metal, or any other suitable structural material. Likewise, further related components of smoking apparatus 10, not otherwise designated already by material preference, can also be constructed from such materials recited above.

FIG. 5 illustrates operating components provided within base 14 and bowl 16 that impart hydrodynamic and cyclonic mixing of fluid and smoke within bowl 16. More particularly, a magnetic stirrer element, or cylindrical rod 60 is provided in a bottom of bowl 16 and a U-shaped horseshoe, or permanent magnet 56 is provided within a housing 50 of base 14. Magnet 56 is driven in rotation via a rotating drive shaft 58 and an electric motor 54. Motor 54 is supported within housing 50 by a cross member, or arm 52 that is affixed at each end to an inner surface of housing 50. Rod 60 magnetically couples with magnet 56 through magnetic coupling of opposite poles to drive rod 60 in rotation within bowl 16, along a bottom surface, thereby imparting rotation of water 35 within bowl 16. Such action serves to impart cyclonic mixing within bowl 16 of water 35 and smoke that is drawn using the hydrofoil smoke entrainment apparatus 74 depicted below in reference to FIG. 7. According to one construction, rod 60 is a cylindrical rod segment of magnetic material, a permanent magnet, having a magnetically neutral shell or covering, such as a thin plastic coating which protects the rod from corrosion. The term "magnetically neutral" refers to the ability of the material to suitably pass magnetic flux lines so as to not interfere with magnetic coupling between magnet 56 and rod 60. Optionally, rod 60 can be constructed from any suitable magnetic or magnetizable material, with or without a coating. Further details of one suitable construction for the mixing system provided by motor 54 and magnets 56 and 60 are provided in U.S. Pat. No. 2,350,534, herein incorporated by reference.

FIG. 5 further illustrates construction details of smoke withdrawal apparatus 26. Apparatus 26 includes exit port 42, hose 44, end fittings 68 and 72, mouthpiece 46 and threaded nuts 66 and 70. According to one construction, hose 44 is an expandable plastic hose having a helical wire contained, laminated, or embedded within the plastic, similar to a common expandable vacuum cleaner hose. End fittings 68 and 72 are plastic fittings each having a complementary helical ridged outer end surface that is fitted within a respective top end portion of hose 44. Mouthpiece 46 is press-fit about a tubular end portion of fitting 72. End fitting 68 has a similar complementary helically ridged outer end surface at an upper end that is also fitted within a respective bottom end portion of hose 44. Furthermore, end fitting 68 has a male threaded portion at a bottom end and a nut 70 has complementary threads configured to mate with the threaded portion on fitting 68 to trap a bottom end of fitting 68 to a bottom tubular portion of exit port 42. A central male threaded portion of exit port 42 receives a complementarily threaded nut 66, trapping exit port 42 to baffle plate 84 (see FIG. 6) and holding a radially outwardly extending flange of exit port 42 against a top surface of cover 18.

Figure 6:
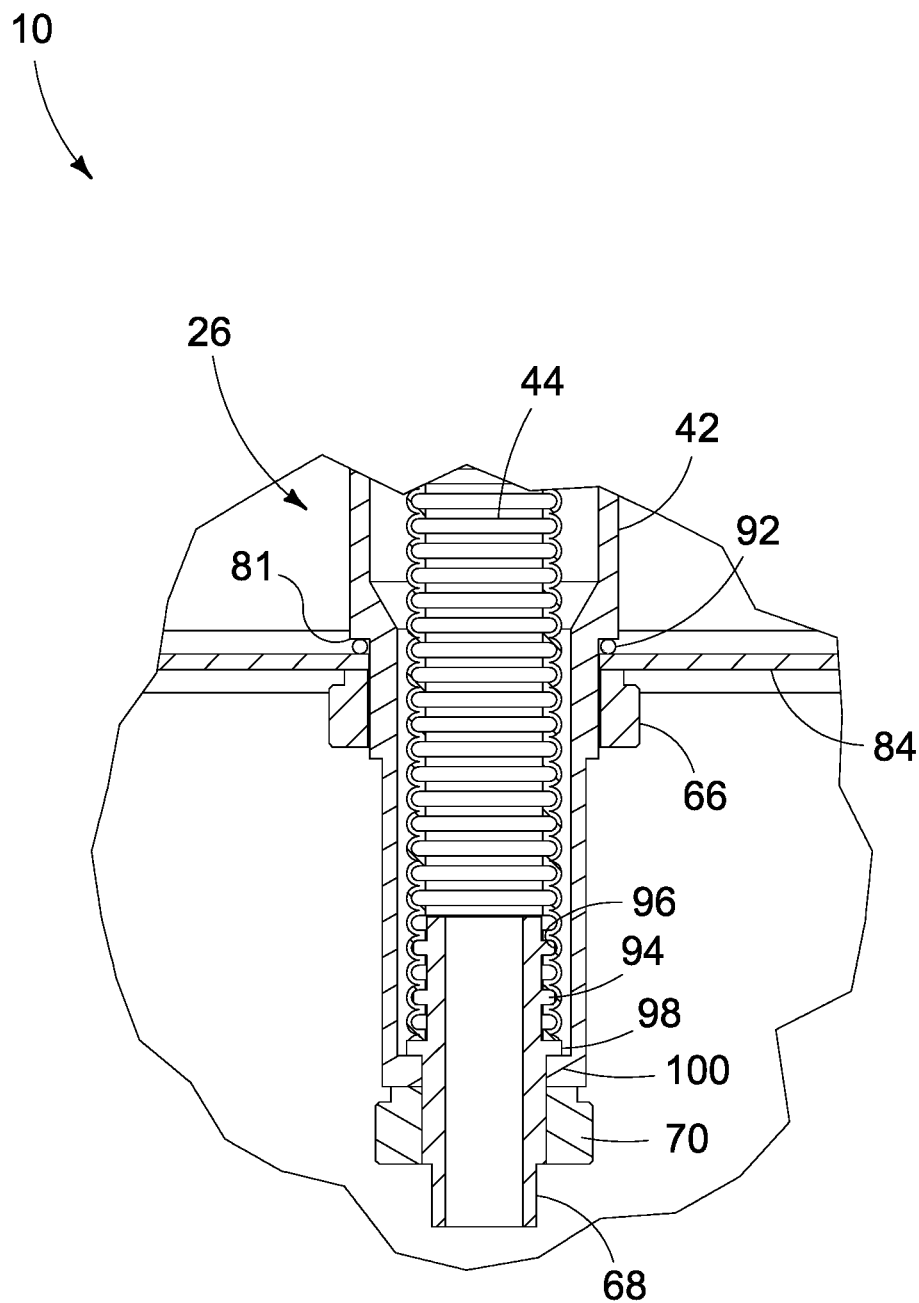
FIG. 6 is a vertical sectional view taken from encircled region 6 of FIG. 5 illustrating a smoke filtering and fluid entraining bubbler having a hydrodynamic flow deflecting body.

As shown in greater detail in FIG. 6, a synthetic rubber o-ring 92 is provided between a reduced-diameter flange 81 on exit port 42, and nut 66 is threaded about a threaded portion of exit port 42, trapping baffle plate against o-ring 92 and exit port 42 so as to provide a seal there between. Additionally, hose 44 is shown in simplified view as a series of undulating round rings, but it is understood that hose 44 is actually a helical series of undulations and that fittings 68 and 72 each have a complementary helical ridge that inter-fits with undulations in hose 44, for example, fitting 68 has a helical ridge 94 that inter-fits within helical groove 96 in hose 44 (of FIG. 6) on apparatus 26. A radially outwardly extending flange 98 on fitting 68 co-acts with nut 70 in order to trap a bottom end of fitting 68 and hose 44 to a bottom end of exit port 44. A top end of hose 44, namely, mouthpiece 46 and distal end of hose 44, can then be stretched away from cover 18 by stretching hose 44 in order to enable a user that is placing mouthpiece 46 in their mouth to draw, or suck smoke from within apparatus 10.

Figure 7:
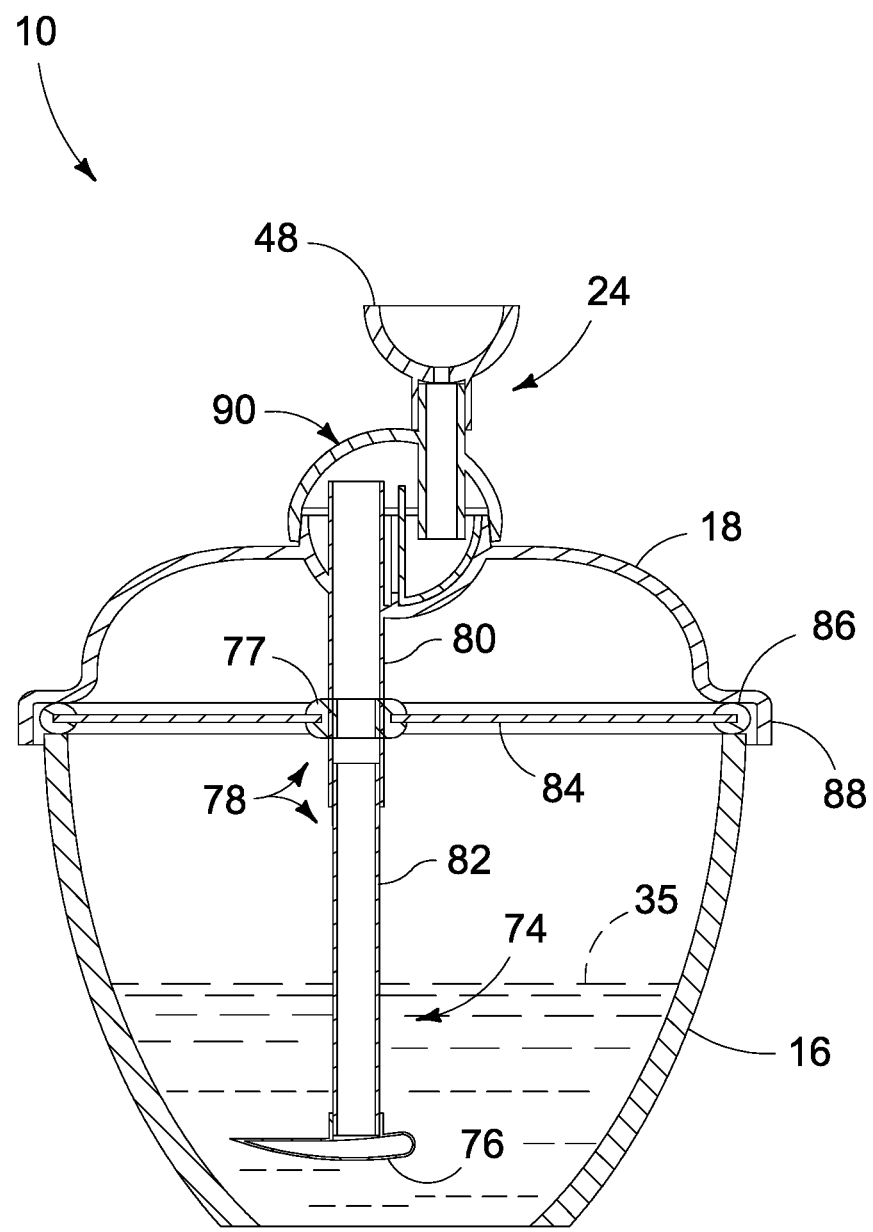
FIG. 7 is an enlarged sectional view taken along line 7-7 of FIG. 2.

FIG. 7 illustrates the arrangement of smoke and ash filtration apparatus 24 and hydrofoil smoke entrainment apparatus 74. In operation, a user inhales through mouthpiece 46 (see FIG. 5) so as to draw a vacuum inside of bowl 16, which also helps draw smoke into bowl 16 from cup 48. As a result, smoke and air are drawn into bowl 16 from cup 48, with the smoke being generated from burning plant material that has been placed within bowl 48. A separating chamber 90 is provided in filtration apparatus 24 for separating smoke and ash. Any ash is left in bowl 12 or chamber 90, while smoke passes from bowl 48, through chamber 90, through intake pipe assembly 78, and through an inverted hydrofoil 76.

Hydrofoil 76 of FIG. 7 is radially offset from a central axis of bowl 16 in order to place hydrofoil 76 in a moving flow of water such that a further vacuum is continuously generated within bowl 16 by water moving over the opposed surfaces of hydrofoil 76, causing a vacuum on the slower speed upper surface of hydrofoil 76. An array of ports 79 (see FIGS. 11 and 11A) are provided in the lower, high speed surface of hydrofoil 76 where smoke and air drawn from bowl 48 are then entrained, or mixed with water that is moving in a cyclonic, or circular path within bowl 16. According to one construction, ports 79 each comprise a static port.

Although shown in the shape of a hydrofoil 76, it is understood that nearly any shaped body can be placed into a fluid flow with a surface portion positioned relative to surrounding fluid flow so as to impart suction to one or more static ports. It is understood that even flat plates, round objects, irregularly shaped bodies, even a figurine, can be placed into a fluid flow with an angle of attack that generates suction at one or more static ports to draw a mixture of air and smoke to be entrained and mixed in a fluid. Such concept is known to enable fighter aircraft to fly upside down relative to their otherwise upwardly facing classic wing design.

According to one construction, hydrofoil 76 is an inverted hydrofoil having a lower surface that is a high speed airfoil surface, and a top surface that is a relatively lower speed airfoil surface. Such relative speeds impart pressure differences between the two surfaces and generates a vacuum on the high speed surface at ports 79 (of FIGS. 11 and 11A), serving to draw a vacuum within chamber 90 and draw smoke from bowl 48. Pursuant to such one construction, hydrofoil 76 has an angle of attack (in the inverted position) with a leading edge raised approximately 3.5 degrees relative to the trailing edge, thereby imparting a downward redirection of water and smoke that is moving past hydrofoil 76 in a cyclonic flow pattern. Such angle imparts further mixing elevationally within the rotating (or cyclonically moving) fluid of bowl 16, providing even further mixing and entrainment of smoke and water. Such mixing is coupled with dispersion of smoke into a very large number of very small bubbles (resulting from a large number of exit ports 79 (see FIGS. 11 and 11A) to increase total surface area for a given amount of smoke, or gas, within water 35 of bowl 16, which contributes to increased cooling of such smoke. A resulting fine dispersion of small bubbles (of smoke and air) within circulating water 35 creates an elevated rate of heat transfer, imparting greater cooling to such smoke. The resulting cooled smoke bubbles to the surface of water 35 and collects within bowl 16, above a top surface of water 35.

Water is moved, or rotated cyclonically so as to pass over the leading edge of hydrofoil 76 toward the trailing edge, as shown in FIG. 7, pursuant to rotation of stirrer element 60 (see FIG. 5). Water 35 is provided at a level within bowl 16, beneath a sealed baffle plate 84 to provide a collection volume of air and smoke between a top surface of water 35 and baffle plate 84 that is at least as great as a typical user's normal lung capacity. The position of hydrofoil 76 can then be adjusted by way of interference-fit and inter-nested upper tube 80 and lower tube 82 of intake pipe assembly 78. A resilient rubber grommet 77 is provided in a cylindrical hole within baffle plate 84, and tube 80 is received in interference fit there through so as a to provide a seal there between. Baffle plate 84 includes a circumferentially-extending edge gasket 86 formed of elastic rubber material sized to be received in assembly in compressed and sealed engagement within a circumferential rim flange 88 of cover 18, between cover 18 and a top circumferential edge of bowl 16.

Figure 8:
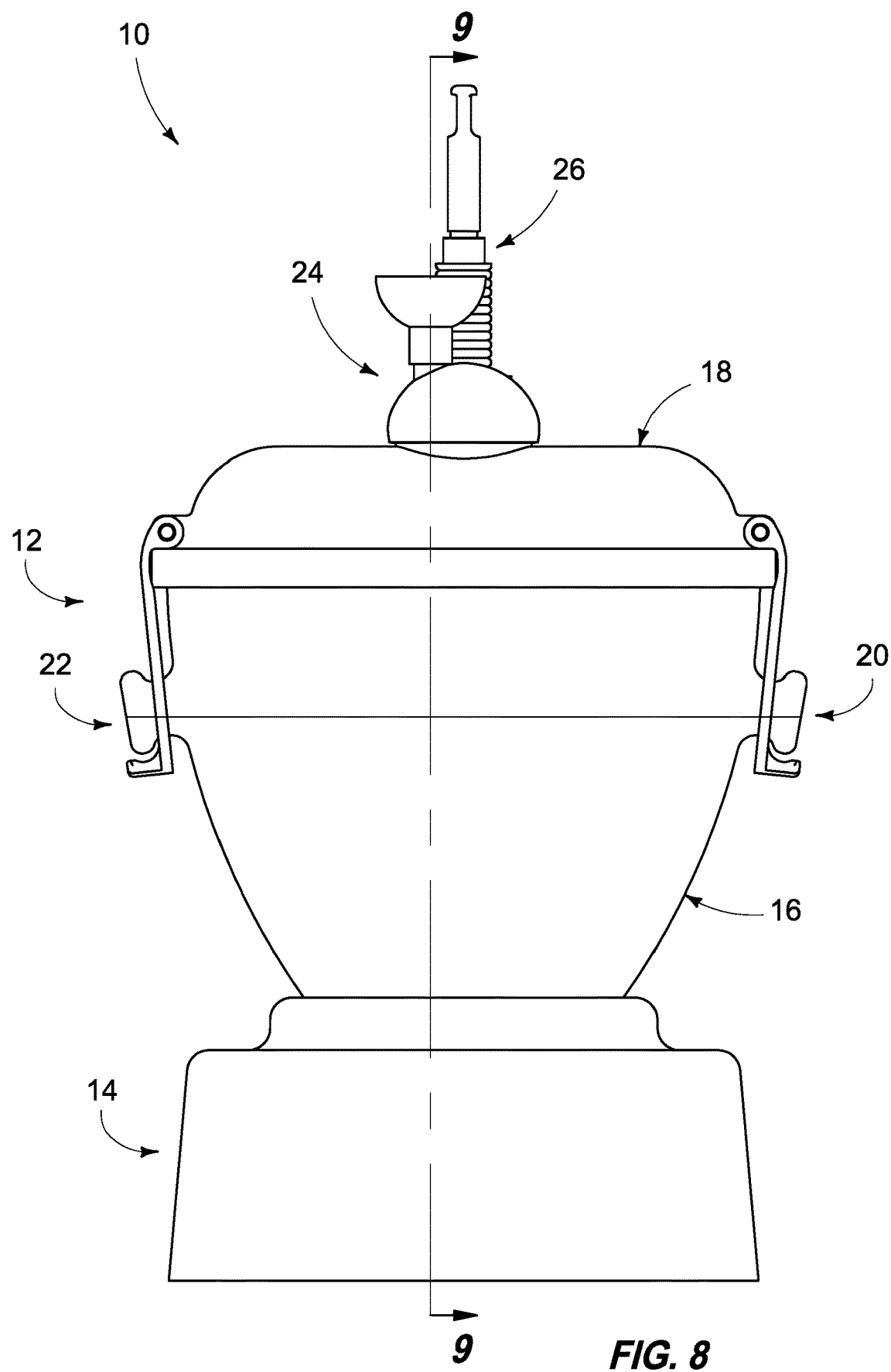
FIG. 8 is a back elevational view of the water pipe of FIGS. 1-4.
Figure 9:
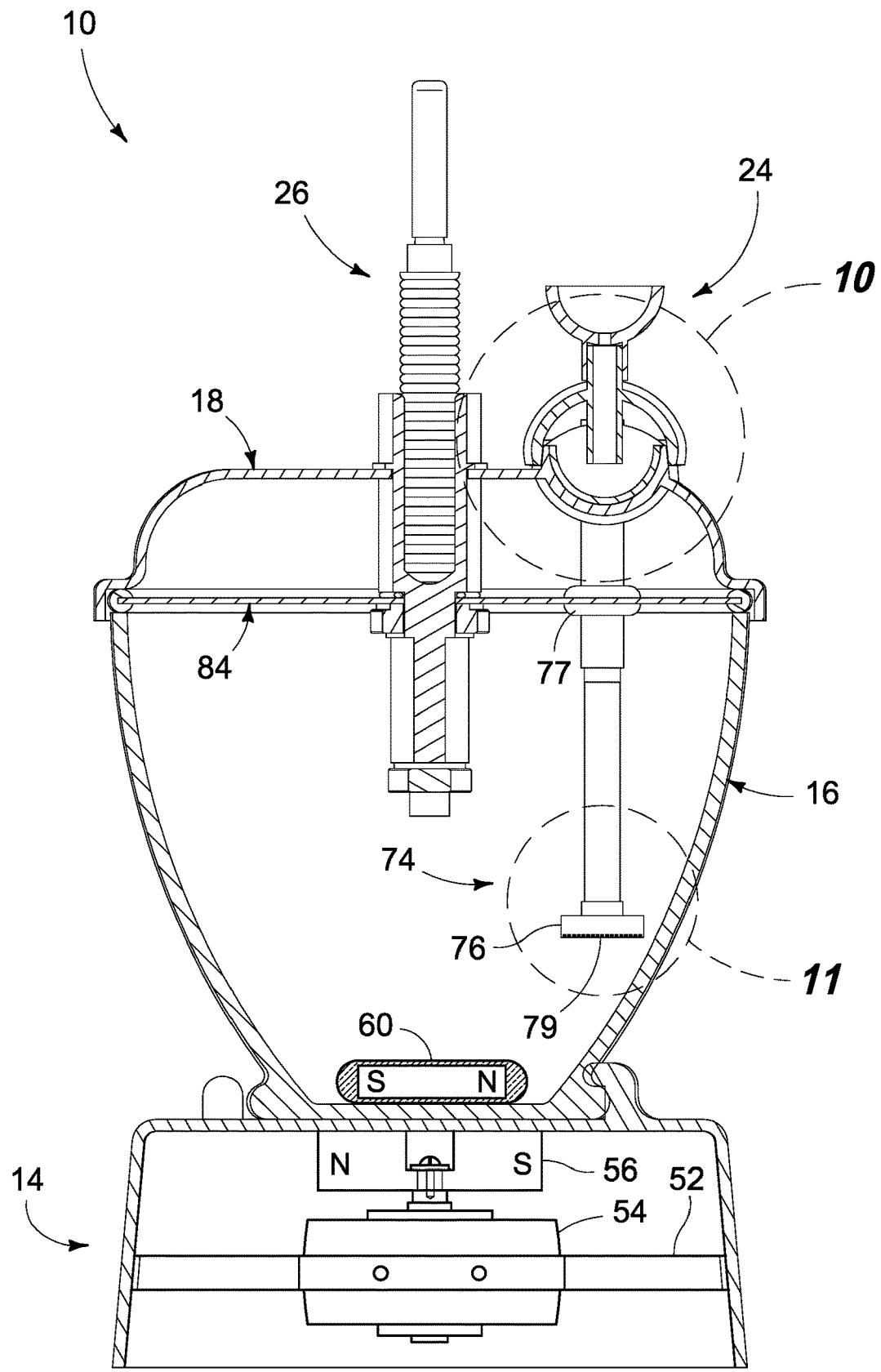
FIG. 9 is a vertical sectional view taken along line 9-9 of FIG. 8.

FIG. 8 further illustrates smoke and ash filtration apparatus 24 atop cover 18 along with smoke withdrawal apparatus 26 of bowl assembly 12 from apparatus 10. Cover latch assemblies 20 and 22 removably secure cover 18 atop bowl 16 and base 14. As shown in cross-section in FIG. 9, smoke and ash filtration apparatus 24 draws in smoke and air via apparatus 24 within bowl 16 for delivery via exit ports 79, hydrofoil 76 of hydrofoil, and smoke entrainment apparatus 74 within bowl 16, resulting from the flow of fluid over hydrofoil 76.

Figure 10:
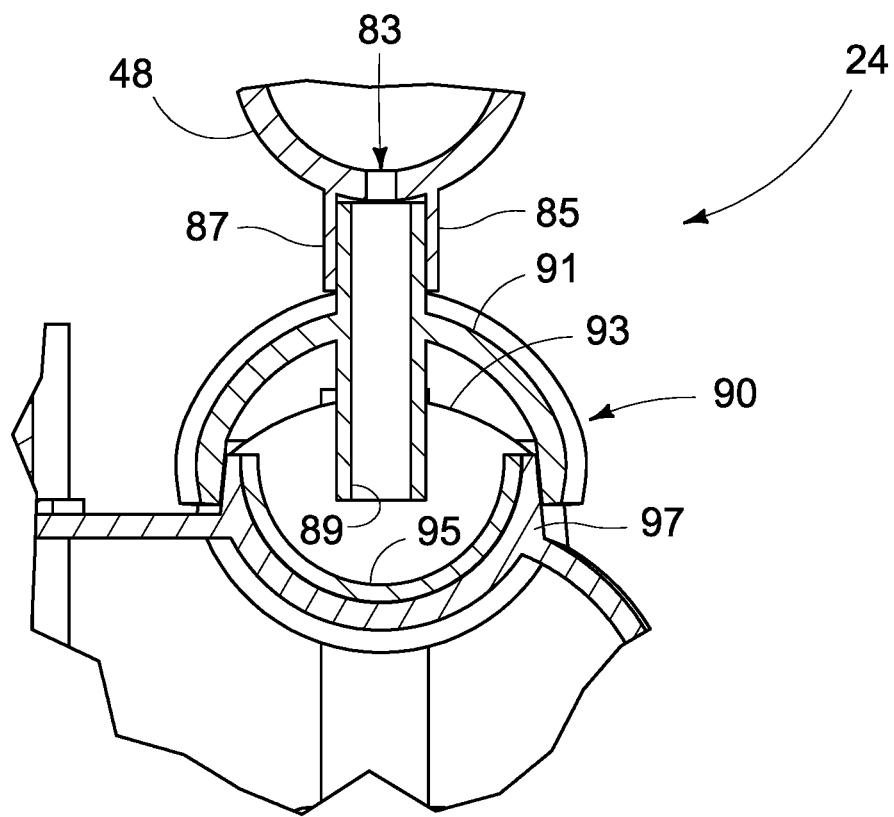
FIG. 10 is an enlarged vertical sectional view taken from encircled region 10 of FIG. 9.

As shown in further detail in FIG. 10, smoke and ash filtration apparatus 24 includes semi-spherical bowl 48 and ash and smoke separating chamber 90. Bowl 48 is affixed atop chamber 90 with a cylindrical outer tubular end portion 85 seated coaxially in snug fit about a complementary tubular end portion 87 of a semi-cylindrical cap 91. Cap 91 retains a pan-shaped (or bowl-shaped) spring clip 93 that locks into an inner lip flange formed integrally within a semi-cylindrical dish 97 provided in the cover. A removable ash cup 95 seats within a portion of dish 97, beneath an exit port 89 of tube 87. Further details of apparatus 24 are shown in exploded view as utilized in an alternative embodiment depicted and described in FIG. 15 below.

Figure 11:
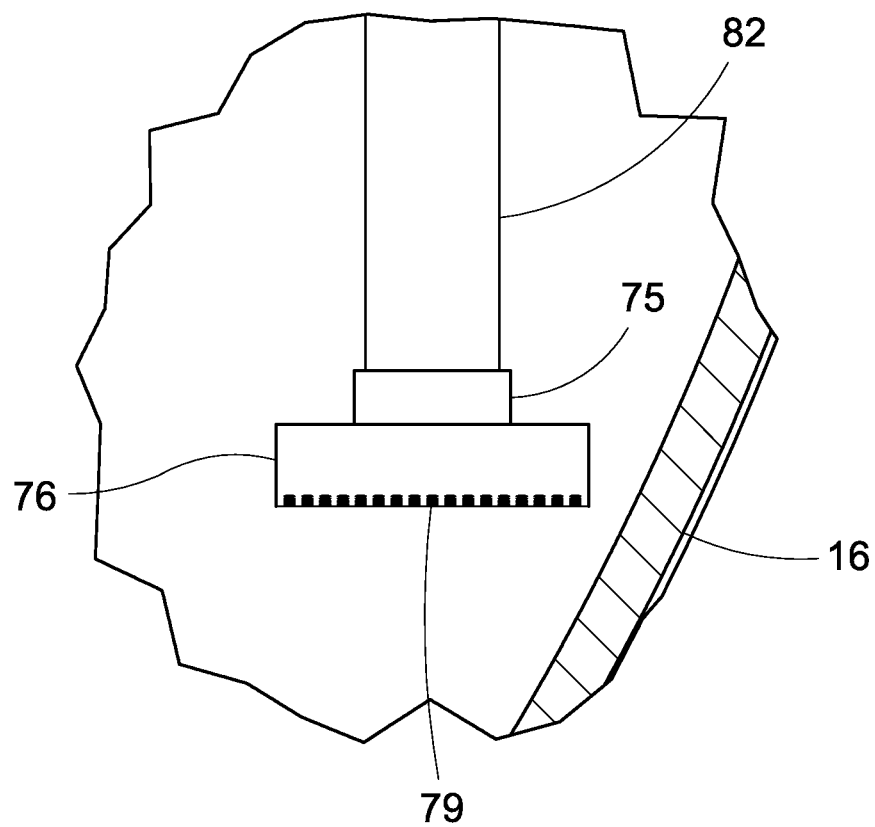
FIG. 11 is an enlarged vertical sectional view taken from encircled region 11 of FIG. 9.

FIG. 11 illustrates hydrofoil 76 along a viewing direction corresponding with a direction of fluid flow over foil 76. Foil 76 is shown with the leading edge in end view, and with a cylindrical top collar 75 sized to fit coaxially over an end of tube, or pipe 82. Ports 79, further depicted in an array in FIG. 11A, are provided along a bottom surface of hydrofoil 76.

Figure 11A:
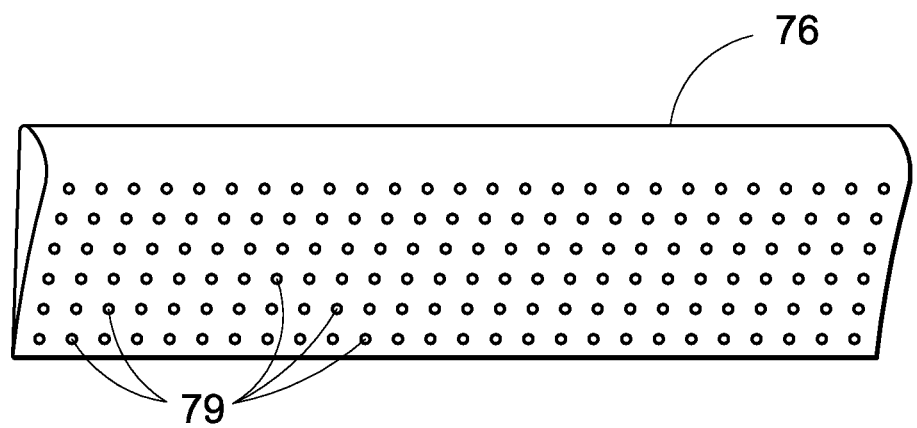
FIG. 11A is a bottom view of the hydrofoil of FIG. 11.

As shown in FIG. 11A, ports 79 communicate with a hollow interior of hydrofoil 76 which further communicates with an inside of pipe 82 (of FIG. 11). FIG. 11A is a bottom left view taken from a left side angle to show the foil shape of hydrofoil 76 and the rectangular array of ports 79.

Figure 12:
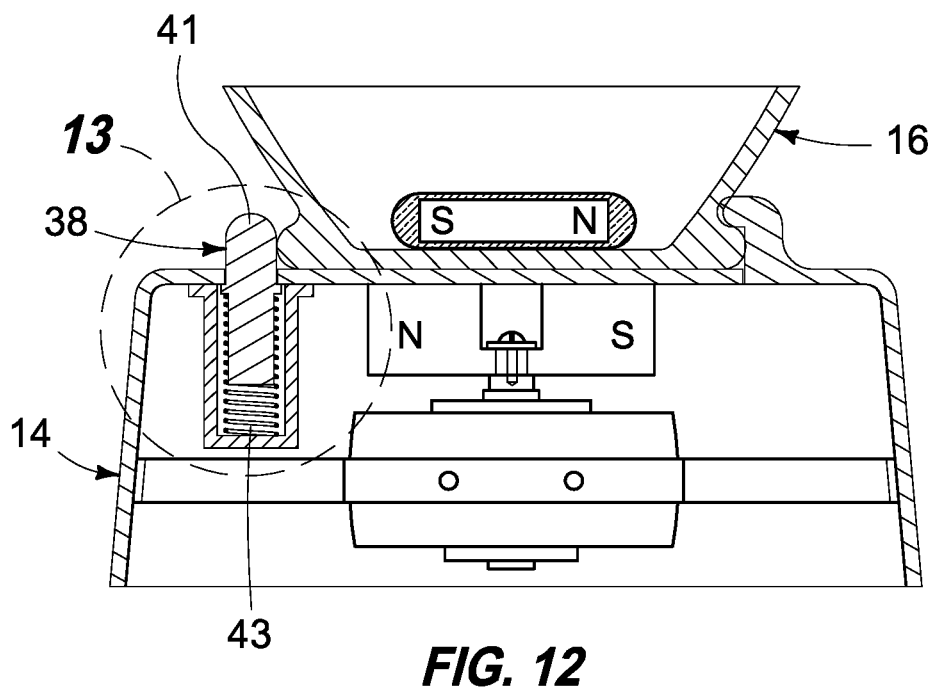
FIG. 12 is partial vertical sectional view of the base and lower bowl taken along line 12-12 of FIG. 3.
Figure 13:
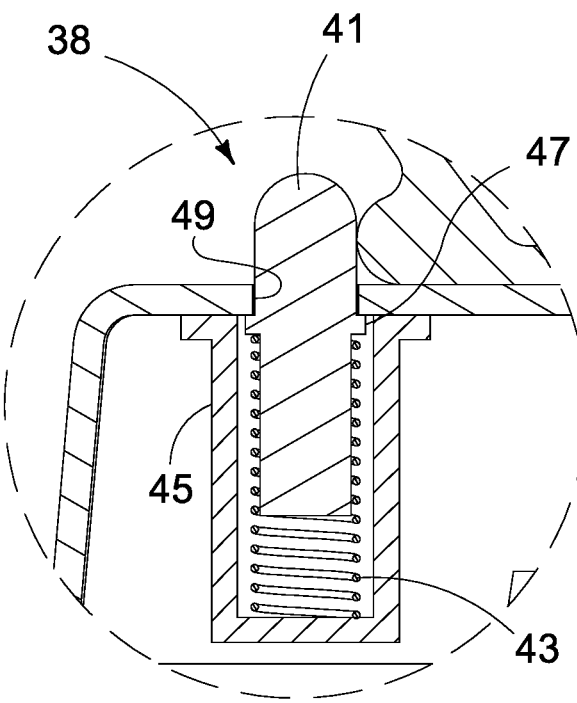
FIG. 13 is a vertical sectional view of the latch assembly from within encircled region 13 of FIG. 12 used to secure the bowl to the base.

FIGS. 12 and 13 illustrate construction details of latch assembly 38 for retaining bowl 16 atop base 14. More particularly, a plunger, or post 41 is spring-biased upwardly by a captured coil spring 43 to retain bowl 16 locked atop base 14. By physically downwardly depressing plunger 41 to compress spring 43, a base flange of bowl 16 is enabled to be cleared over plunger 41, facilitating removal and/or insertion of bowl 16 over base 14. As shown in FIG. 13, plunger 41 has a radially-outwardly extending flange 47 that forms a seat beneath a cylindrical aperture 49 of the base housing. A cylindrical cap-shaped housing 45 is affixed, in assembly to a bottom surface of the base housing using ultrasonic welds for the case when housing 45 and the base housing are constructed from plastic. Other alternative constructions are suitable including sheet metal components that are welded or brazed together having any of a number of suitable alternative geometries having rectangular, square or elliptical cross-sections. Spring 43 is received in a compressed state, in assembly, between flange 47 and a bottom inner surface of housing 45. Optionally, any of a number of fasteners or adhesive can be used to affix housing 45 to the housing 50 (see FIG. 5) of base 14 including threaded male and female base members, fasteners, latches, rivets, screws, bolts, clasps or any other suitable mechanism configured for mating and demating such components. Even furthermore, such components can optionally be integrally formed together as a single unit.

FIGS. 14-22 illustrate an alternative embodiment cyclonically cooled and filtered water pipe 110. Water pipe 110 is essentially the same as water pipe 10 (of FIGS. 1-13), with the exception of a magnetic cover latch assembly 120 and the addition of a finger loop 149 integrally formed in the body of outlet 146 of extensible smoke withdrawal apparatus 126. More particularly, latch assembly 120 includes a cover magnetic latch member 121 provided on cover 118 and a bowl magnetic latch member 123 provided on bowl 116. Magnetic cover latch assembly 120 includes magnetic latch pairs 125, 127 and 129. Tube assembly 142 extends through and above cover 118 a greater distance than tube assembly 42 (of FIG. 1). Details of smoke and ash filtration apparatus 24, base 14 and plunger 38 are the same as those described generally with reference to the embodiment of FIGS. 1-13.

Figure 15:
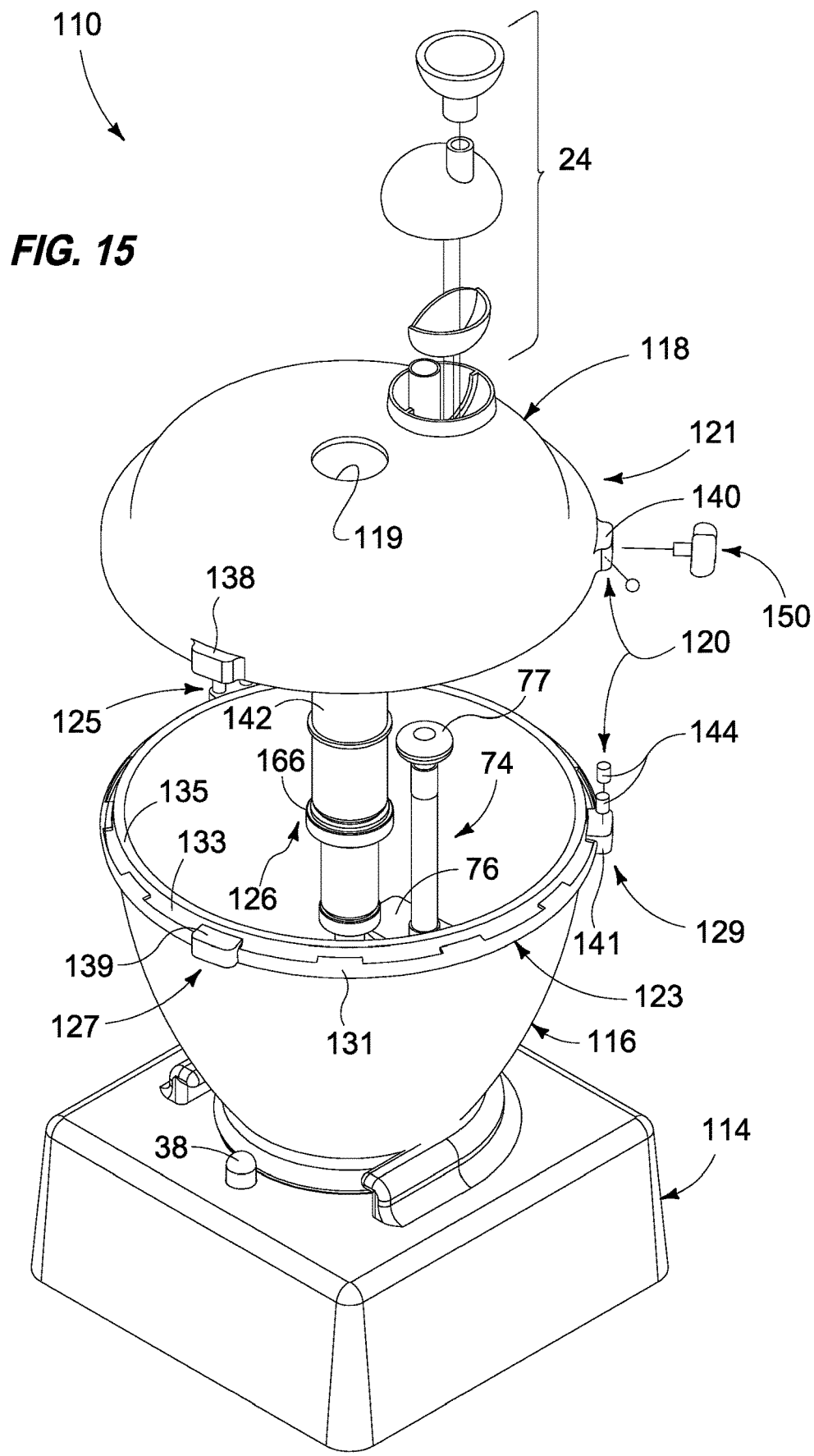
FIG. 15 is an exploded perspective view with portions removed of the water pipe of FIG. 14.

FIG. 15 illustrates details of magnetic cover latch assembly 120 for removably securing cover 118 to bowl 116. More particularly, latch pairs 125, 127 and 129 include mating pairs of lugs 138, 139; 140, 141; and 142, 143 (see FIG. 19) which cooperate in pairs in order to magnetically couple together cover 118 to bowl 116 through respective latch members 121 and 123. A release latch 150 on lug 140 is rotated to separate latch members 121 and 123, enabling release of cover 118 from atop bowl 116. Lugs 139, 141 and 143 (see FIG. 19) are integrally formed onto a circumferential ring 131 that is secured on a lip flange 133 of bowl 116 by bending down a circumferential array of rectangular tabs that overly flange 133 in a radial inward direction. Flange 133 is perpendicular to a top flange 135 on bowl 116. Lugs 139, 141 and 143 are formed from magnetizable material, such as a ferrous metal capable of being magnetized when placed in contact with a permanent magnet, such as individual rare-earth magnets 144 that are pressed into cylindrical bores in lugs 138, 140 and 142 (see FIG. 19).

Optionally, latch assembly 150 for holding cover 118 onto bowl 116 of FIG. 15 can be formed from any of a number of fasteners or adhesive that can be used to affix cover 118 atop bowl 116 including threaded male and female members, fasteners, latches, rivets, screws, bolts, clasps or any other suitable mechanism configured for mating and demating such components.

Figure 14:
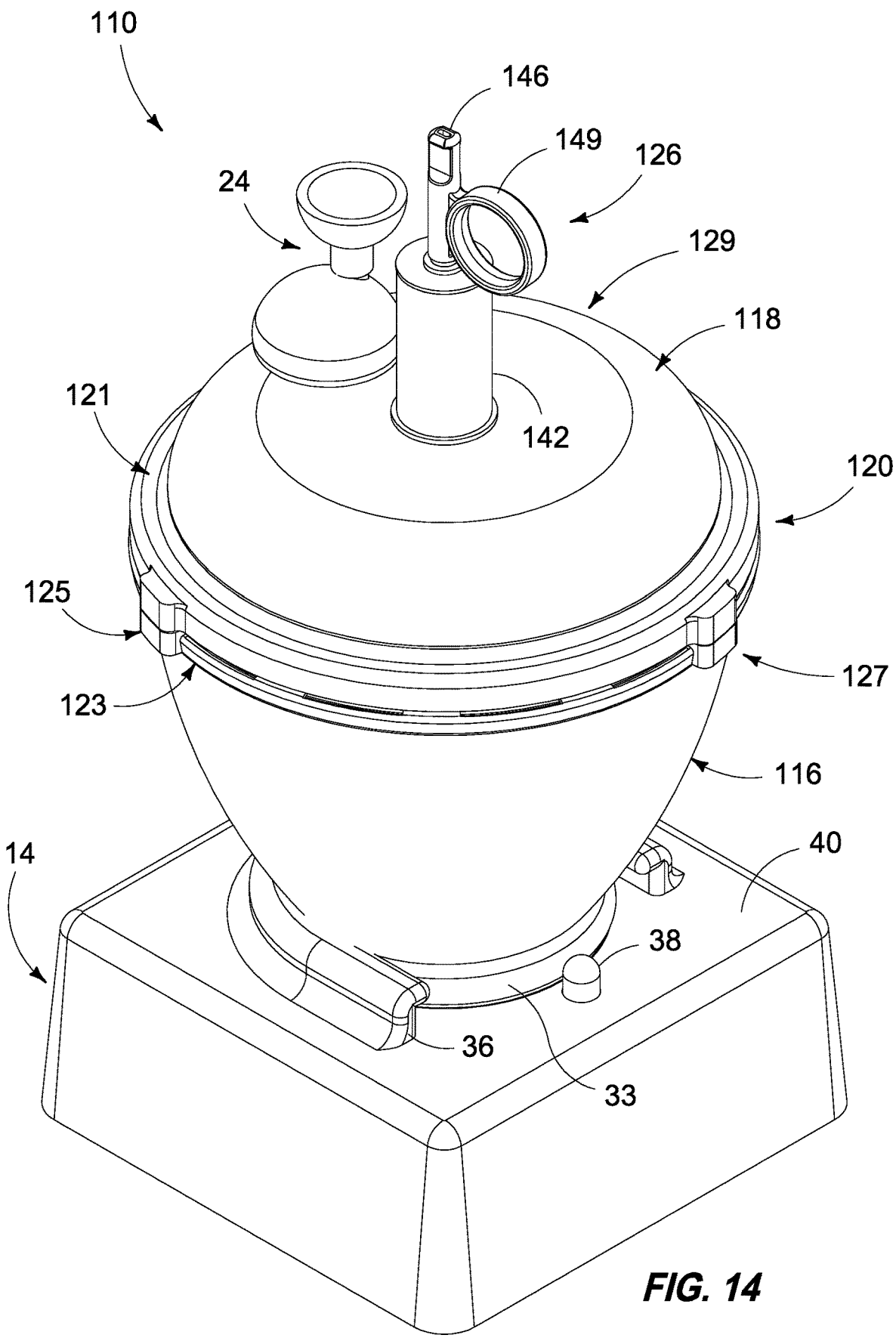
FIG. 14 is a perspective view from above illustrating a cyclonically cooled and filtered water pipe according to another embodiment having a magnetically latching cover assembly.
Figure 16:
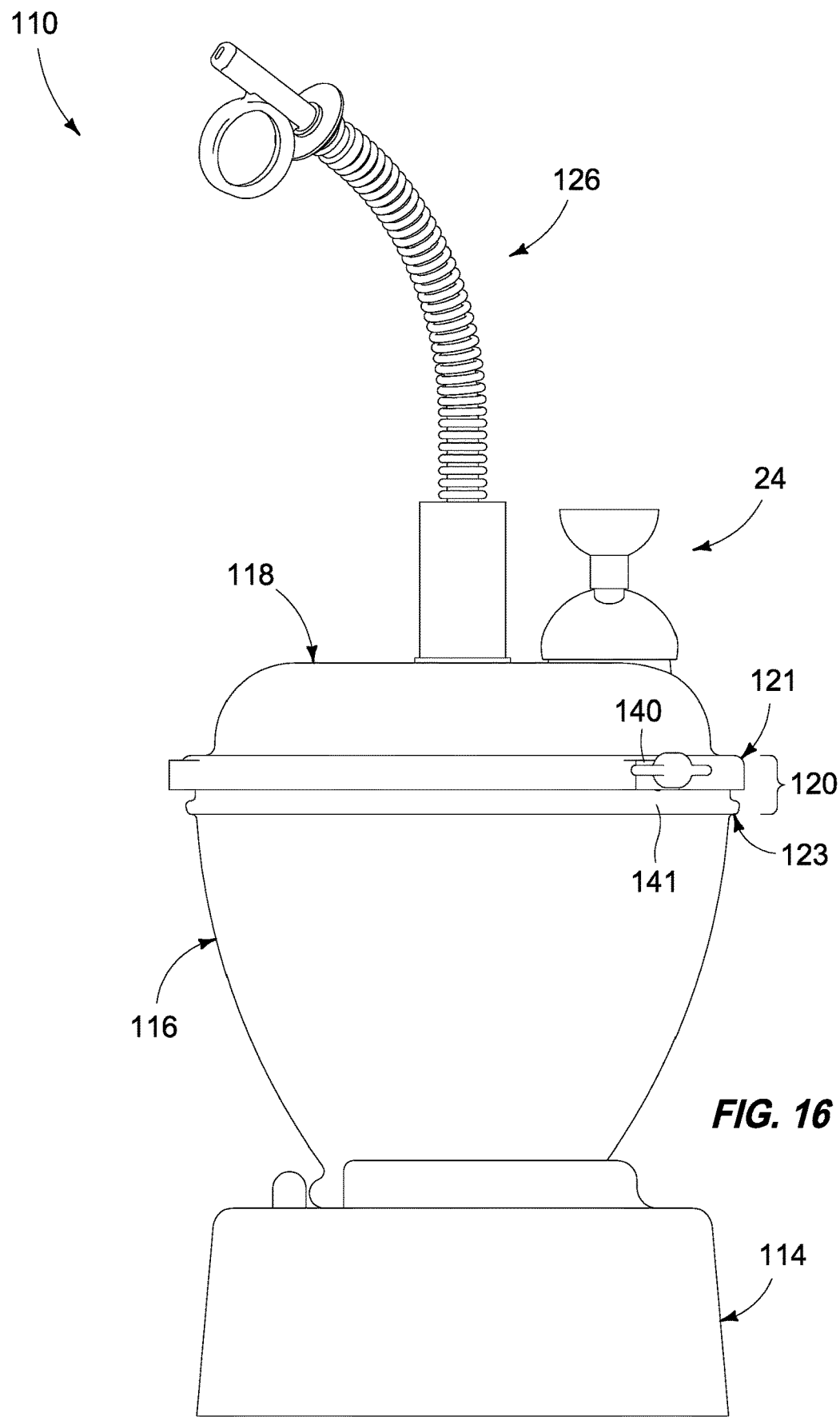
FIG. 16 is a right side elevational view of the water pipe of FIGS. 14-15.
Figure 17:
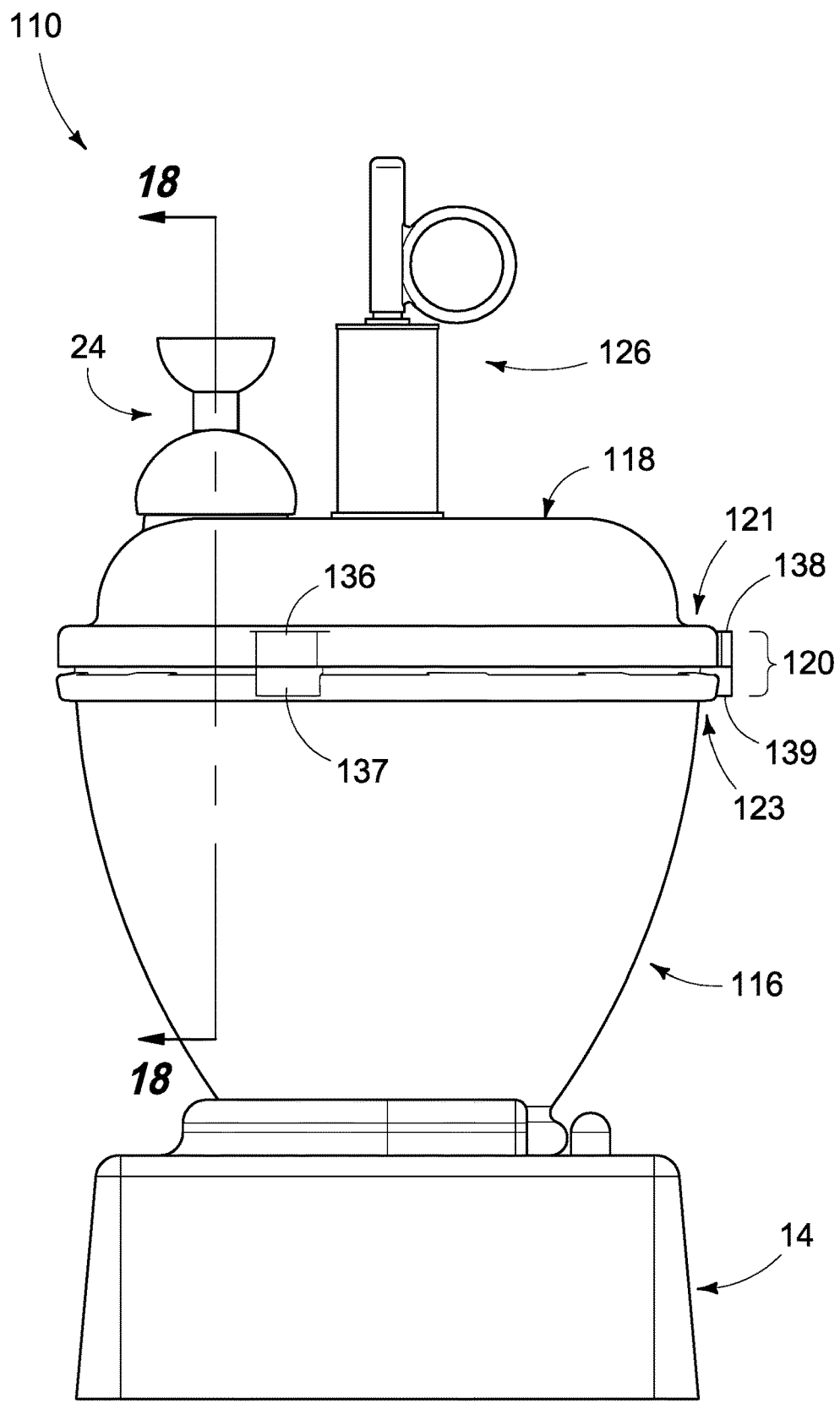
FIG. 17 is a left side elevational view of the water pipe of FIGS. 14-16.
Figure 18:
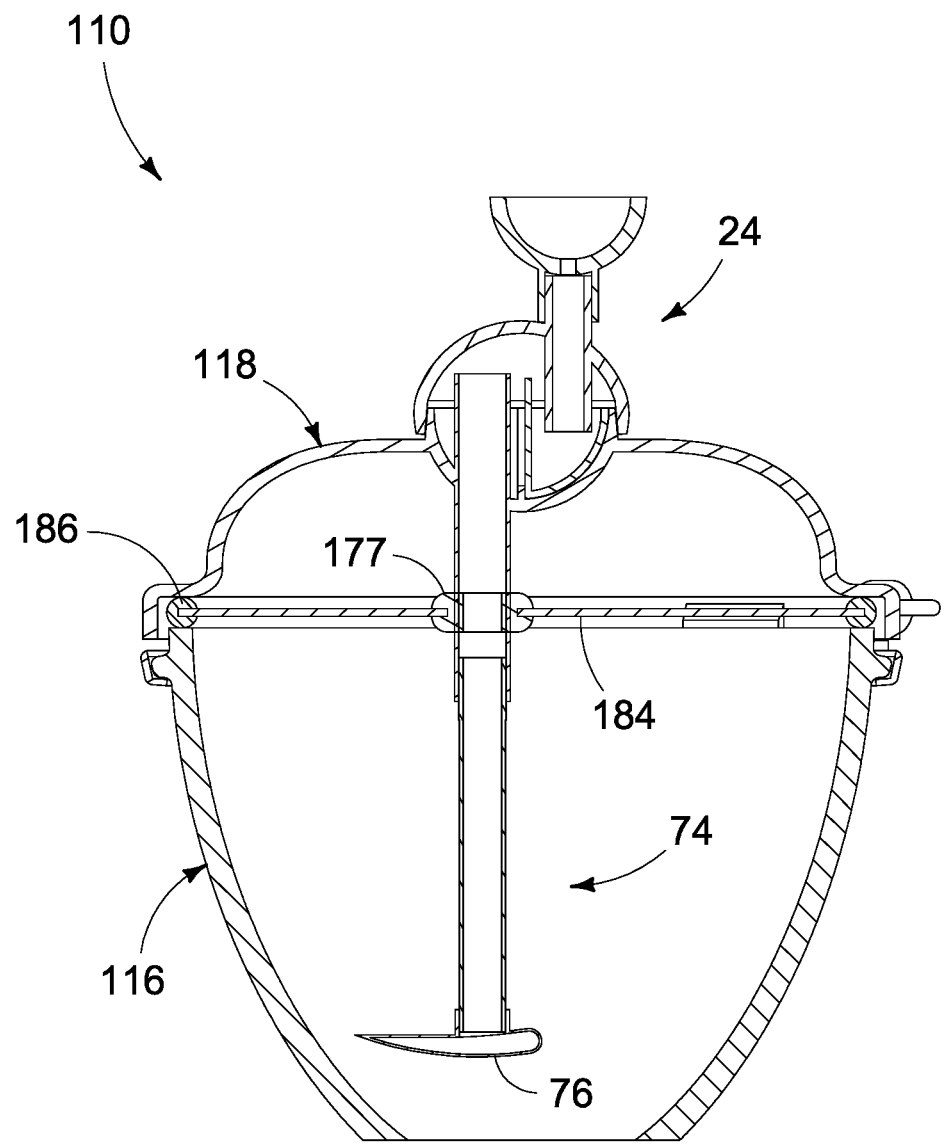
FIG. 18 is a vertical sectional view of the water pipe of FIGS. 14-17 taken along line 18-18 of FIG. 17.
Figure 19:
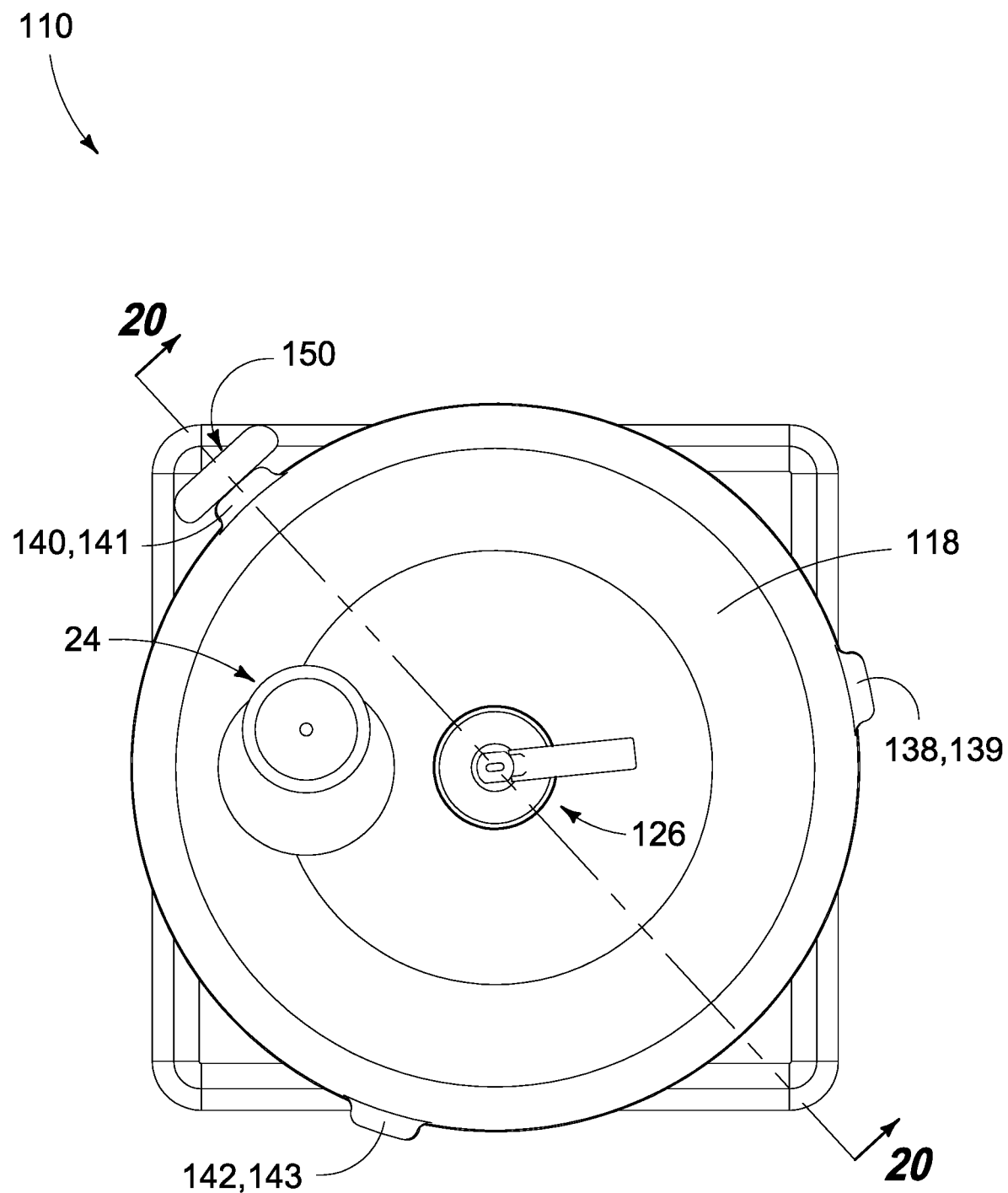
FIG. 19 is a plan view from above of the water pipe of FIGS. 14-18.
Figure 20:
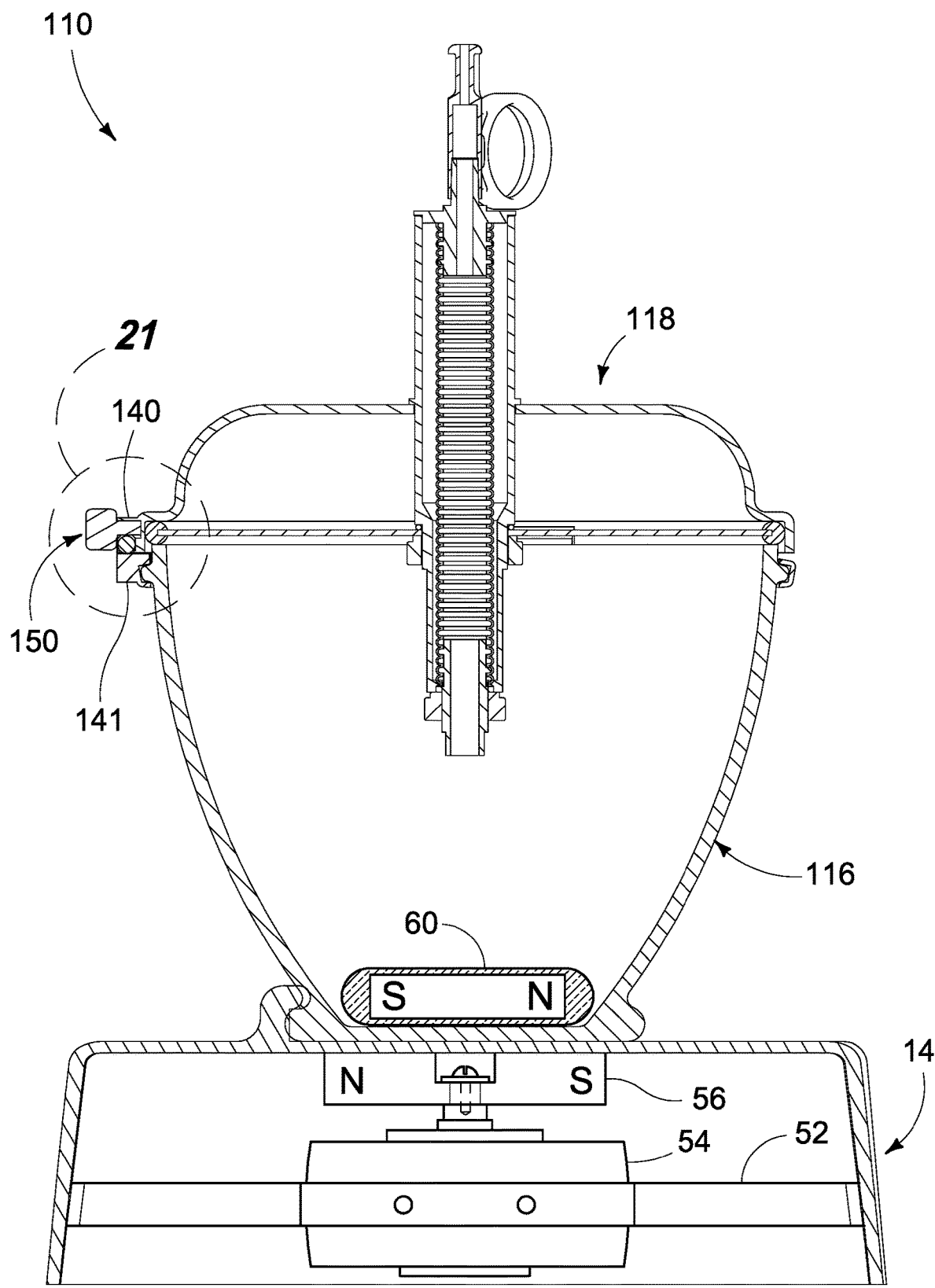
FIG. 20 is a vertical sectional view of the water pipe of FIGS. 14-19 taken along line 20-20 of FIG. 19.
Figure 21:
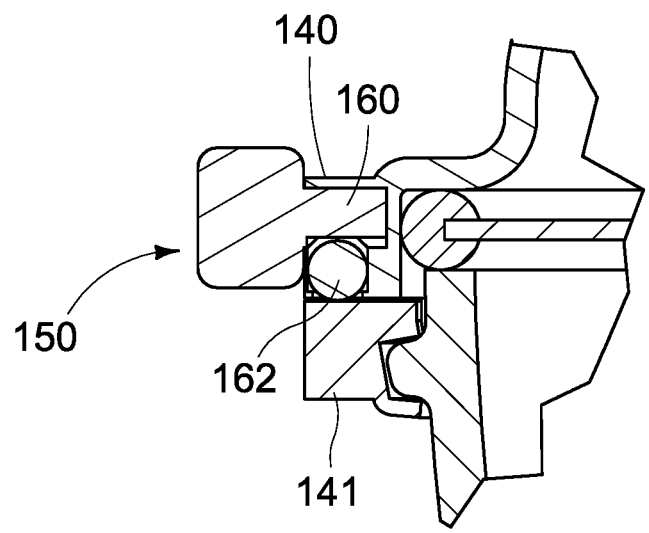
FIG. 21 is an enlarged vertical sectional view taken from encircled region 21 of FIG. 20.
Figure 23:
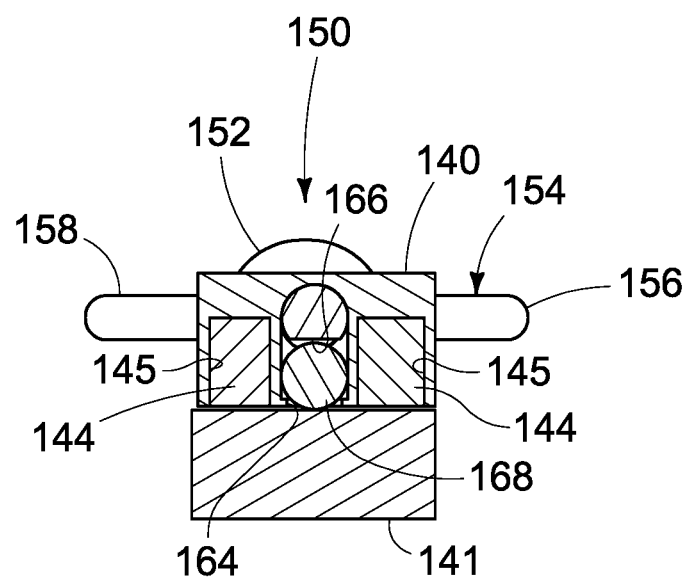
FIG. 23 is a vertical sectional view of the magnetic latch release taken along line 23-23 of FIG. 22.
Figure 22:
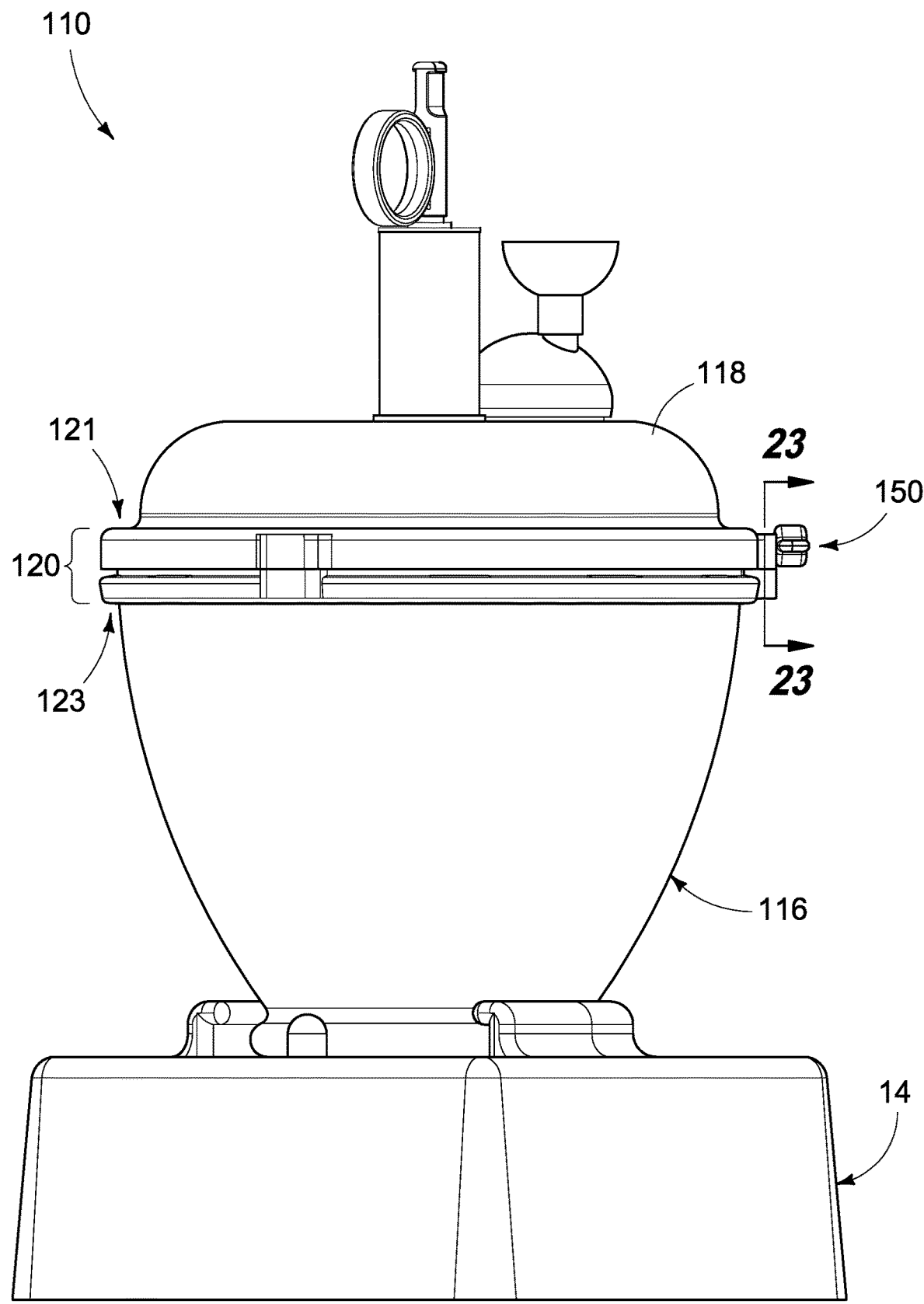
FIG. 22 is an elevational view taken in a direction perpendicular to a magnetic latch release for the water pipe of FIGS. 14-21.

As shown in FIG. 16, extensible smoke withdrawal apparatus 126 can be extended for use and has a flexible plastic hose body with an accordion-style hose that can extend and retract in length. Apparatus 126 can then also be fully retracted as shown in FIGS. 14 and 17.

In compliance with the statute, embodiments of the invention have been described in language more or less specific as to structural and methodical features. It is to be understood, however, that the entire invention is not limited to the specific features and/or embodiments shown and/or described, since the disclosed embodiments comprise forms of putting the invention into effect. The invention is, therefore, claimed in any of its forms or modifications within the proper scope of the appended claims appropriately interpreted in accordance with the doctrine of equivalents.

The invention claimed is:

1. A hydrodynamically cooled and filtered smoking apparatus, comprising:
   a housing having at least one wall portion providing a chamber forming a radial inner surface of revolution having a central axis and configured to contain a fluid for circulation therein;
   an inlet pipe having an inlet configured to draw in smoke from a source and an outlet provided within the chamber beneath a top surface of the contained fluid configured to deliver the smoke into the chamber for entrainment within the fluid;
   a stirring mechanism provided in the housing and driven to induce cyclonic circulation of the fluid and the smoke in the chamber; and
   a flow deflecting body radially offset outwardly from the central axis of the chamber within the cyclonic circulation of the fluid and having a high pressure top surface and a low pressure bottom surface and a suction surface provided in the low pressure bottom surface with at least one aperture provided in the suction surface and fluidly communicating with the inlet pipe, the suction surface oriented in the fluid to generate hydrodynamic downward force to draw smoke into the fluid and aerate the fluid by entraining the smoke in the fluid as bubbles and downwardly redirect the smoke and the fluid.

2. The smoking apparatus of claim 1, wherein the stirring mechanism comprises a magnetic stirrer provided in the chamber for rotation and configured to stir and agitate the liquid.

3. The smoking apparatus of claim 2, wherein the stirring mechanism further comprises a magnetic drive unit provided outside of the housing configured to impart magnetic flux through a wall of the container to rotate the magnetic stirrer to stir and mix the smoke and air.

4. The smoking apparatus of claim 2, wherein the magnetic drive unit comprises an energy source for driving magnetic fluxes for a pair of drive magnets on the stirrer.

5. The smoking apparatus of claim 1, further comprising an outlet tube having an inlet within the chamber and above a top surface of the liquid configured to draw in smoke coalescing above the entrained smoke and liquid within the chamber, and an outlet provided outside of the chamber.

6. The smoking apparatus of claim 1, wherein the housing comprises a bowl-shaped side wall and a cylindrical bottom wall contiguous with the side wall.

7. The smoking apparatus of claim 6, wherein the side wall comprises a frustoconically-shaped wall portion.

8. The smoking apparatus of claim 1,
further comprising an ash bowl fluidly communicating with the inlet of the inlet pipe.

9. The smoking apparatus of claim 1, wherein the chamber comprises a surface of revolution defining at least in part a cyclonic chamber.

10. The smoking apparatus of claim 1, wherein the flow deflecting body comprises a hydrofoil body supported in the chamber.

11. The smoking apparatus of claim 10, wherein the suction surface of the hydrofoil comprises an array of apertures spaced apart along the suction surface.

12. A hydrodynamically cooled and filtered smoking apparatus, comprising:
a housing having at least one wall portion providing a chamber configured to contain a fluid for circulation therein;
an inlet pipe having an inlet configured to draw in smoke from a source and an outlet provided within the chamber beneath a top surface of the contained fluid configured to deliver the smoke into the chamber for entrainment within the fluid;
a stirring mechanism provided in the housing and driven to induce circulation of the fluid and the smoke in the chamber; and
a flow deflecting body having a suction surface with at least one aperture provided in the suction surface and fluidly communicating with the inlet pipe, the suction surface oriented in the fluid to generate hydrodynamic force to draw smoke into the fluid and aerate the fluid by entraining the smoke in the fluid as bubbles;
wherein the flow deflecting body comprises a hydrofoil body supported in the chamber in a path of the fluid while in cyclonic circulation, the hydrofoil supported with an angle of attack relative to the fluid with the suction surface provided opposite a pressure surface.

13. The smoking apparatus of claim 12, wherein the suction surface of the hydrofoil comprises an array of apertures spaced apart along the suction surface.

14. The smoking apparatus of claim 12, wherein the hydrofoil body is radially offset outwardly from the central axis of the chamber within the cyclonic circulation of the fluid and has a high pressure top surface, a low pressure bottom surface, and the suction surface provided in the low pressure bottom surface.

15. A cyclonically cooled and filtered smoking water pipe, comprising:
a housing having a chamber having a radial inner surface of revolution about a central axis and configured to contain a liquid for cyclonic circulation therein;
an inlet pipe having an inlet for drawing in a smoke and an outlet provided within the chamber so as to be entrained in a fluid bath therein;
a surface portion having a high pressure top surface and a low pressure bottom surface radially offset from the central axis of the chamber configured to be entrained in the fluid bath and provided in fluid communication with fluid in cyclonic circulation within the chamber;
a static port provided in the surface portion fluidly communicating with the inlet pipe, the surface portion oriented in the fluid to generate a vacuum on the inlet pipe to draw smoke into the fluid and entrain the smoke in the fluid as bubbles; and
a stirring mechanism provided in the housing and driven to induce cyclonic circulation of the fluid and the smoke in the chamber.

16. The water pipe of claim 15, wherein the housing comprises at least one wall portion configured to form a cyclonic chamber.

17. The water pipe of claim 16, wherein the stirring mechanism further comprises a magnetic drive unit provided outside of the housing configured to impart magnetic flux through a wall of the container to rotate the magnetic stirrer to stir and mix the smoke and liquid.

18. The water pipe of claim 15, wherein a plurality of static ports are provided in the surface portion.

19. The water pipe of claim 18, wherein the surface portion is a high speed surface of a hydrodynamic foil provided in fluid communication within the liquid in the chamber.

20. The water pipe of claim 15, wherein the stirring mechanism comprises a magnetic stirrer provided in the chamber for rotation and configured to stir and agitate the liquid.

* * * * *